US009295375B2

(12) United States Patent
Shahinian et al.

(10) Patent No.: US 9,295,375 B2
(45) Date of Patent: Mar. 29, 2016

(54) PROGRAMMABLE SPECTRAL SOURCE AND DESIGN TOOL FOR 3D IMAGING USING COMPLEMENTARY BANDPASS FILTERS

(71) Applicants: Hrayr Karnig Shahinian, Beverly Hills, CA (US); Michael J. Shearn, San Antonio, TX (US); Youngsam Bae, Los Angeles, CA (US); Ronald J. Korniski, Thousand Oaks, CA (US); Eric W. Fritz, Atkinson, NE (US); Allen Ream, Anchorage, AK (US)

(72) Inventors: Hrayr Karnig Shahinian, Beverly Hills, CA (US); Michael J. Shearn, San Antonio, TX (US); Youngsam Bae, Los Angeles, CA (US); Ronald J. Korniski, Thousand Oaks, CA (US); Eric W. Fritz, Atkinson, NE (US); Allen Ream, Anchorage, AK (US)

( * ) Notice: Subject to any disclaimer, the term of this patent is extended or adjusted under 35 U.S.C. 154(b) by 559 days.

(21) Appl. No.: 13/628,788

(22) Filed: Sep. 27, 2012

(65) Prior Publication Data

US 2014/0085420 A1    Mar. 27, 2014

(51) Int. Cl.
*A61B 1/00*    (2006.01)
*A61B 1/045*    (2006.01)
*A61B 1/06*    (2006.01)

(52) U.S. Cl.
CPC ............. *A61B 1/00193* (2013.01); *A61B 1/045* (2013.01); *A61B 1/0646* (2013.01)

(58) Field of Classification Search
CPC ... A61B 1/00193; A61B 1/045; A61B 1/0646
USPC .......................................................... 348/45
See application file for complete search history.

(56) References Cited

U.S. PATENT DOCUMENTS

| 1,960,011 A | 5/1934 | Ives |
| 2,255,631 A | 9/1941 | Shulman |
| 3,870,037 A | 3/1975 | Cadariu et al. |
| 4,651,201 A | 3/1987 | Schoolman |
| 4,759,348 A | 7/1988 | Cawood |
| 4,761,066 A | 8/1988 | Carter |
| 4,873,572 A | 10/1989 | Miyazaki et al. |

(Continued)

FOREIGN PATENT DOCUMENTS

| EP | 0469966 B1 | 2/1992 |
| EP | 1371321 A1 | 12/2003 |

(Continued)

OTHER PUBLICATIONS

Eric Fritz, "High-Speed Generation of Illumination Spectra for a Stereoscopic Endoscope", Aug. 9, 2011, NASA JPL, XP055046123, pp. 1-8.*

(Continued)

*Primary Examiner* — Christopher S Kelley
*Assistant Examiner* — Asmamaw G Tarko

(57) ABSTRACT

An endoscopic illumination system for illuminating a subject for stereoscopic image capture, the illumination system includes a light source which outputs multi-spectral light; first and second light paths configured to transmit the multi-spectral light; and a digital mirror array (DMA) which receives the multi-spectral light and directs the multi-spectral light to a selected one of the first and second light paths. A controller controls the DMA to direct the multi-spectral light to the selected light path in accordance with a time-multiplexing scheme; and/or first and second complementary multi-band bandpass filters (CMBF). The first CMBF may be situated in the first light path and the second CMBF may be situated in the second light path, where the first and second CMBFs filter the multi-spectral light incident thereupon to output filtered light.

20 Claims, 19 Drawing Sheets

(56) References Cited

U.S. PATENT DOCUMENTS

| | | | |
|---|---|---|---|
| 4,877,307 A | 10/1989 | Kalmanash | |
| 4,951,676 A | 8/1990 | Collet-Billon | |
| 5,050,226 A | 9/1991 | Collet-Billon | |
| 5,105,269 A | 4/1992 | Nakamura et al. | |
| 5,192,969 A | 3/1993 | Igarashi et al. | |
| 5,222,477 A | 6/1993 | Lia | |
| 5,305,098 A | 4/1994 | Matsunaka et al. | |
| 5,395,030 A | 3/1995 | Kuramoto et al. | |
| 5,436,655 A | 7/1995 | Hiyama et al. | |
| 5,459,605 A | 10/1995 | Kempf | |
| 5,471,237 A | 11/1995 | Shipp | |
| 5,494,483 A | 2/1996 | Adair | |
| 5,536,234 A | 7/1996 | Newman | |
| 5,540,229 A | 7/1996 | Collet-Billon et al. | |
| 5,547,455 A | 8/1996 | McKenna et al. | |
| 5,603,687 A | 2/1997 | Hori et al. | |
| 5,605,532 A | 2/1997 | Schermerhorn | |
| 5,662,584 A | 9/1997 | Hori et al. | |
| 5,667,473 A | 9/1997 | Finn et al. | |
| 5,697,891 A | 12/1997 | Hori | |
| 5,743,847 A | 4/1998 | Nakamura et al. | |
| 5,751,341 A | 5/1998 | Chaleki et al. | |
| 5,782,752 A | 7/1998 | Lichtman et al. | |
| 5,810,716 A | 9/1998 | Mukherjee et al. | |
| 5,817,014 A | 10/1998 | Hori et al. | |
| 5,823,940 A | 10/1998 | Newman | |
| 5,827,323 A | 10/1998 | Klieman et al. | |
| 5,828,487 A | 10/1998 | Greening et al. | |
| 5,835,194 A | 11/1998 | Morton | |
| 5,841,887 A | 11/1998 | Kuwayama et al. | |
| 5,855,549 A | 1/1999 | Newman | |
| 5,895,350 A | 4/1999 | Hori | |
| 5,928,137 A | 7/1999 | Green | |
| 5,935,057 A | 8/1999 | Lichtman et al. | |
| 5,941,817 A | 8/1999 | Crawford | |
| 5,941,818 A | 8/1999 | Hori et al. | |
| 5,944,654 A | 8/1999 | Crawford | |
| D415,146 S | 10/1999 | Hori | |
| 5,964,696 A | 10/1999 | Mihalca et al. | |
| 5,984,939 A | 11/1999 | Yoon | |
| 5,989,182 A | 11/1999 | Hori et al. | |
| 6,046,727 A | 4/2000 | Rosenberg et al. | |
| 6,050,939 A | 4/2000 | Pak Wai | |
| 6,066,090 A | 5/2000 | Yoon | |
| 6,086,528 A | 7/2000 | Adair | |
| 6,159,146 A | 12/2000 | El Gazayerli | |
| 6,191,809 B1 | 2/2001 | Hori et al. | |
| 6,211,848 B1 | 4/2001 | Plesniak et al. | |
| 6,223,100 B1 | 4/2001 | Green | |
| 6,277,064 B1 | 8/2001 | Yoon | |
| RE37,356 E | 9/2001 | Hori et al. | |
| 6,290,649 B1 | 9/2001 | Miller et al. | |
| 6,292,221 B1 | 9/2001 | Lichtman | |
| 6,306,082 B1 | 10/2001 | Takahashi et al. | |
| 6,313,883 B1 | 11/2001 | Thaler | |
| 6,419,626 B1 | 7/2002 | Yoon | |
| 6,445,814 B2 | 9/2002 | Iijima et al. | |
| 6,450,948 B1 | 9/2002 | Matsuura et al. | |
| 6,450,950 B2 | 9/2002 | Irion | |
| 6,517,479 B1 | 2/2003 | Sekiya et al. | |
| 6,593,957 B1 | 7/2003 | Christie | |
| 6,624,935 B2 | 9/2003 | Weissman et al. | |
| 6,647,792 B2 | 11/2003 | Ogawa | |
| 6,731,988 B1 | 5/2004 | Green | |
| 6,817,973 B2 | 11/2004 | Merril et al. | |
| 6,832,984 B2 | 12/2004 | Stelzer et al. | |
| 6,916,286 B2 | 7/2005 | Kazakevich | |
| 6,976,956 B2 | 12/2005 | Takahashi et al. | |
| 6,980,676 B2 | 12/2005 | Pineau | |
| 6,991,602 B2 | 1/2006 | Nakazawa et al. | |
| 6,997,871 B2 | 2/2006 | Sonnenschein et al. | |
| 7,043,062 B2 | 5/2006 | Gerard et al. | |
| RE39,342 E | 10/2006 | Starks et al. | |
| 7,153,259 B2 | 12/2006 | Matsuzawa et al. | |
| 7,154,527 B1 | 12/2006 | Goldstein et al. | |
| 7,241,262 B2 | 7/2007 | Adler et al. | |
| 7,553,277 B2 | 6/2009 | Hoefig et al. | |
| 7,601,119 B2 | 10/2009 | Shahinian | |
| 7,621,869 B2 | 11/2009 | Ratnakar | |
| 2002/0030678 A1 | 3/2002 | Ostermann | |
| 2002/0049367 A1 | 4/2002 | Irion et al. | |
| 2002/0154215 A1 | 10/2002 | Schechterman et al. | |
| 2003/0053744 A1* | 3/2003 | Makio | 385/18 |
| 2003/0125608 A1 | 7/2003 | Igarashi | |
| 2003/0174208 A1 | 9/2003 | Glukhovsky et al. | |
| 2003/0229270 A1* | 12/2003 | Suzuki et al. | 600/178 |
| 2003/0233024 A1 | 12/2003 | Ando | |
| 2004/0019255 A1 | 1/2004 | Sakiyama | |
| 2004/0070667 A1 | 4/2004 | Ando | |
| 2004/0249367 A1 | 12/2004 | Saadat et al. | |
| 2005/0065657 A1 | 3/2005 | Green | |
| 2005/0065658 A1 | 3/2005 | Green | |
| 2005/0119530 A1 | 6/2005 | Douglas et al. | |
| 2005/0228230 A1 | 10/2005 | Schara et al. | |
| 2005/0234296 A1 | 10/2005 | Saadat et al. | |
| 2005/0234297 A1 | 10/2005 | Devierre et al. | |
| 2005/0261548 A1 | 11/2005 | Machiya et al. | |
| 2005/0278711 A1 | 12/2005 | Silva et al. | |
| 2006/0015008 A1 | 1/2006 | Kennedy | |
| 2006/0111614 A1 | 5/2006 | Saadat et al. | |
| 2006/0224040 A1 | 10/2006 | Khait et al. | |
| 2006/0247495 A1 | 11/2006 | Bacher et al. | |
| 2007/0055103 A1 | 3/2007 | Hoefig et al. | |
| 2007/0112256 A1* | 5/2007 | Terakawa et al. | 600/178 |
| 2007/0173689 A1 | 7/2007 | Ozaki et al. | |
| 2007/0249932 A1 | 10/2007 | Shahinian | |
| 2007/0255100 A1 | 11/2007 | Barlow et al. | |
| 2008/0281154 A1 | 11/2008 | Gono et al. | |
| 2008/0284982 A1 | 11/2008 | Richards et al. | |
| 2009/0062662 A1* | 3/2009 | Zuluaga | 600/478 |
| 2009/0137893 A1* | 5/2009 | Seibel et al. | 600/407 |
| 2009/0187072 A1 | 7/2009 | Manohara et al. | |
| 2010/0006549 A1* | 1/2010 | Pahk et al. | 219/121.76 |
| 2011/0115882 A1* | 5/2011 | Shahinian et al. | 348/45 |

FOREIGN PATENT DOCUMENTS

| | | |
|---|---|---|
| EP | 1854420 A1 | 11/2007 |
| EP | 1880657 A1 | 1/2008 |
| EP | 1989990 A1 | 11/2008 |
| JP | 04-021105 | 1/1992 |
| JP | 06-202004 | 7/1994 |
| JP | 06-237892 | 8/1994 |
| JP | 10-010468 | 1/1998 |
| JP | 2000-052289 | 2/2000 |
| WO | 93/13916 A1 | 7/1993 |
| WO | 96/35975 A1 | 11/1996 |
| WO | 99/57900 A1 | 11/1999 |
| WO | 20001050927 A2 | 8/2000 |
| WO | 00/61009 A1 | 10/2000 |
| WO | 2002037142 A2 | 5/2002 |
| WO | 2003098913 A2 | 11/2003 |
| WO | 20051030328 A2 | 4/2005 |
| WO | 20051031433 A1 | 4/2005 |
| WO | 20051120327 A2 | 12/2005 |
| WO | 20081033356 A2 | 3/2008 |

OTHER PUBLICATIONS

Allen Ream, "Project Report: Reducing Color Rivalry in Imagery for Conjugated Multiple Bandpass Filter Based Stereo Endoscopy", Aug. 2011, NASA JPL, XP055046122, pp. 1-9.*

Youngsam Bae, Harish Manohara, Victor E. White, and Kirill V. Shcheglov, "Stereo Imaging Miniature Endoscope", Jun. 2011, NASA Tech Briefs, pp. 6-7.*

Y.S. Heo, "Illumination and Camera Invariant Stereo Matching," Computer Vision and Pattern Recognition, 2008. CVPR 2008. IEEE Conference, vol., No., pp. 1-8, 23-28 Jun. 2008.

J.L. Garb, "Using GIS for spatial analysis of rectal lesions in the human body," International Journal of Health Geographics, 2007, 6:11, Published online Mar. 15, 2007 doi: 10.1186/1476-072X-6-11. PMCID: PMC1839078 BioMed Central Ltd.

(56) References Cited

OTHER PUBLICATIONS

J.P. Rice, "A hyperspectral image projector for hyperspectral imagers," SPIE vol. 6565 65650C, (2007).
J.P. Rice, "Hyperspectral image projectors for radiometric applications," BIPM and IOP Publishing Ltd, Metrologia 43 (2006) S61-S65.
J.P. Rice, "Development of hyperspectral image projectors," SPIE vol. 6297, 629701, (2006).
J.M. Medina, "Binocular interactions in random chromatic changes at isoluminance," Opt. Soc. Am., 2006, vol. 23, No. 2, pp. 239-246.
A. Szold, "Seeing is believing-Visualization systems in endoscopic surgery (video, HDTV, stereoscopy, and beyond)," Surgical Endoscopy, 19:55, pp. 730-733, Springer, 2005.
U. D. A Mueller-Richter,"Possibilities and limitations of current stereo-endoscopy," Journal of Surgical Endoscopy, Springer, New York, ISSN 0930-2794 (Print) 1432-2218 (Online) Issue vol. 18, No. 6, Jun. 2004, 18: pp. 942-947.
M.A. Weissman, "Stereo parallax and Disnparity in Single-Lens Stereoscopy," Stereoscopic Displays and Virtual Reality Systems VII, SPIE 3987, pp. 312-320, Apr. 2000.
G.A. Lester, "Ferroelectric liquid crystal device for a single camera stereoscopic endoscope system," Electronics Letters, 1997, vol. 33, No., 10, pp. 857-858.
G.L. Zimmerman, "Perception at Equiluminance: An Adaptive Model of Motion Metamers," Circuits and Systems, 1994, Proceedings of the 37th Midwest Symposium on , vol. 1, No., pp. 577-580 vol. 1, Aug 3-5, 1994.
Y. Takemura, "Stereoscopic Video Movie Camera Using 300k Pixel IT-CCD Sensors," IEEE Transactions on Consumer Electronics, Feb. 1991, vol. 37, No. 1, pp. 39-44.
E. Badique, "Use of color image correlation in the retrieval of gastric surface topography by endoscopic stereopair matching," Applied Optics, 1988, vol. 27, No. 5, pp. 941-948.
N. Ohyama, "Compensation of motion blur in CCD color endoscope images," Opt. Soc. Am., 2006, Applied Optics, 1987, vol. 26, No. 5, pp. 909-912.
P. Breedveld and M. Wentink, "Eye-hand coordination in laparoscopy—an overview of experiments and supporting aids," Min Invas Ther & Allied Technol 2001: 155-162, 10(3).
Keijirou Itakura, et al., "A 1-mm 50 k-Pixel IT CCD Image Sensor for Miniature Camera System," IEEE Transactions On Electron Devices, Jan. 2000, 65-70, vol. 47, No. 1.
Jacques Duparré, et al., "Thin compound-eye camera," Applied Optics, May 20, 2005, pp. 2949-2956, vol. 44, No. 15.
Jun Tanida, et al., "Color imaging with an integrated compound imaging system," Optics Express, Sep. 8, 2003, 2019-2117, vol. 11, No. 18.
Jun Tanida, et al., "Thin observation module by bound optics (TOMBO): concept and experimental verification," Applied Optics, Apr. 10, 2001, 1806-1813, vol. 40, No. 11.
Ikeda, M., Sagawa, K., "Binocular color fusion limit," J. of the Optical Society of America, 69(2), 316-321, (Feb. 1979).
Dudley, D., Duncan, W. M., Slaughter, J., "Emerging digital miromirror device (DMD) applications," Proceedings of SPIE 4985, 14-25 (2003).
Hovis, J. K., "Review of Dichoptic Color Mixing," Optometry and Vision Science, 66(3), 181-190 (1998).
Lambooij, M., Ijsselsteijn, W., "Visual discomfort and visual fatigue of stereoscopic display: A review," J. of Imaging science and technology, 53(3), 030201 (2009).
DooHyun Lee and InSo Kweon, "A Novel Stereo Camera System by a Biprism," IEEE Transactions On Robotics And Automation, 16(5), 528-541, (Oct. 2000).
Mikko Kyto, Mikko Nuutinen, Pirkko Oittinen, "Method for measuring stereo camera depth accuracy based on stereoscopic vision," OAalto University School of Science and Technology, Department of Media Technology, Otaniementie 17, Espoo, Finland.

Qin, D., Takamatsu, M., Nakashima, Y., Qin, X., "Change of wavelength difference limit for binocular color fusion with wavelength and brightness of stimuli," J. of Light and Visual Environment, 30(1), 43-45 (2006).
Jung, Y. J., Sohn, H., Lee, S., Ro, Y. M., and Park, H. W., "Quantitative measurement of binocular color fusion limit for non-spectral colors.," Optics express, 19(8), 7325-7338 (2011).
Planar Systems Inc., "SD1710 Pruduct User's Guide," 1-12 (2005).
CRI Varispec, "Liquid Crystal Tuneable Filters," 1-12 (2005).
Avi Yaron, Mark Shechterman and Nadav Horesh, "Blur spot limitations in distal endoscope sensors," Proc. SPIE 6055, Stereoscopic Displays and Virtual Reality Systems XIII, 605509 (Jan. 27, 2006).
Researchers Work on Snake-Like 'Rescue Robots', downloaded on Apr. 20, 2006 from http://www.foxnew5.com/printer_friendly_story/O,3566, 192430,OO.htm.
NASA Infrared Camera Helps Surgeons Map Brain Turners, Jul. 15, 2004,downloaded on Apr. 24, 2006 from http://www.jpl.nasa.gov/news/news.cfm?release=20D4-183.
Fung et al., "A Case Study of 3D Stereoscopic VS. 20 Monoscopic Tele-Reality in . . . " IEEE/RSJ International Conference on Intelligent Robots and Systems, 2005, pp. 181-6.
Nain et al., "Three-Dimensional Nanoscale Manipulation and Manufacturing Using Proximal Probes: Controlled Pulling of Polymer . . . " IEEE Int Conf Rob Autom vol. 1,2004, pp. 434-9.
Lytle et al., Adapting a Teleoperated Device for Autonomous Control Using Three-Dimensional Positioning sensors: . . . Automation in Construction, vol. 13, 2004, pp. 101-118.
Mezouar et al., Robustness of Central Catadioptric Image-based Visual . . . • IEEE RSJ Int. Conf. IntelL Robots and Syst. IROS, vol. 2, Sep. 28 - Oct. 2, 2004, Sendai, JP, pp. 1389-1394.
Murakami et al., "Automatic Insertion Work. Based on Visual Measurement and Contact Force Estimation" Proc IEEE Int Conf Rob Autom, vol. 4, May 2002, pp. 4167-4172.
Trivedi et al., "A Vision System for Robotic Inspection and Manipulation", DE90 005412, Univ of Tennessee, Revised Mar. 1989. pp. 1-12.
Nguyen et al., "30 Model Control of Image Processing" in JPL, California Inst. of Tech., Proceedings of the NASA Conference on Space Telerobotics, vol. 3, pp. 213-222 May 2000.
Stiel et af. Digital Flashing Tomosynthesis: A Promising Technique for Angiocardiographic ScreeningD IEEE Transactions on Medical Imaging, Jun. 1993, No. 2, NY, pp. 314-321.
Fritz, Eric., "High Speed Generation of Illumination Spectra for a Stereoscopic Endoscope", http://hdl.handle.net/2014/42272, Nasa Undergraduate Student Research Program (USRP), Pasadena, California, Aug. 9, 2011, pp. 1-8, Retrieved from Internet: URl: http://trs-new.jpl.nasa.gov/dspace/bitstream/2014/42272/1/11-3811.pdf.
Ream, Allen, "Project report: reducing color rivalry in imagery for conjugated multiple bandpass filter based stereo endoscopy", http://hdl.handle.net/2014/42276, NASA Undergraduate Student Research Program (USRP), Pasadena, California, Aug. 2011, pp. 1-9, Retrieved from Internet: URL: http://trs-new.jpl.nasa.gov/dspace/bitstream/2014/42276/1/11-3803.pdf.
J.P. Rice et al., "Hyperspectral image compressive projection algorithm," SPIE vol. 7334 pp. 733414-1, XP055046293, ISSN: 0277-786X, DOI: 10.1117/12.818844, (Apr. 27, 2009).
Sam Bae et al, "Toward a 3D endoscope minimally invasive surgery", SPIE Newsroom, Sep. 21, 2011, pp. 1-3, XP055046098, DOI: 10.1117/2.1201109.003810.
NASA'S Jet Propulsion Laboratory et al: "Stereo Imaging Miniature Endoscope", Internet Citation, Jun. 30, 2011, pp. 6-7, XP002687431, Retrieved from the Internet: URL:http://ntrs.nasa.gov/archive/nasa/casi.ntrs.nasa.gov/20110012587_2011013131.pdf [retrieved on Dec. 3, 2012].
Ronald Korniski et al: "3D imaging with a single-aperture 3-mm objective lens: concept, fabrication, and test", Proceedings of SPIE, vol. 8144, Sep. 14, 2011, p. 812904, XP055046246, ISSN: 0277-786X, DOI: 10.1117/12.894110.

* cited by examiner

500C

500D

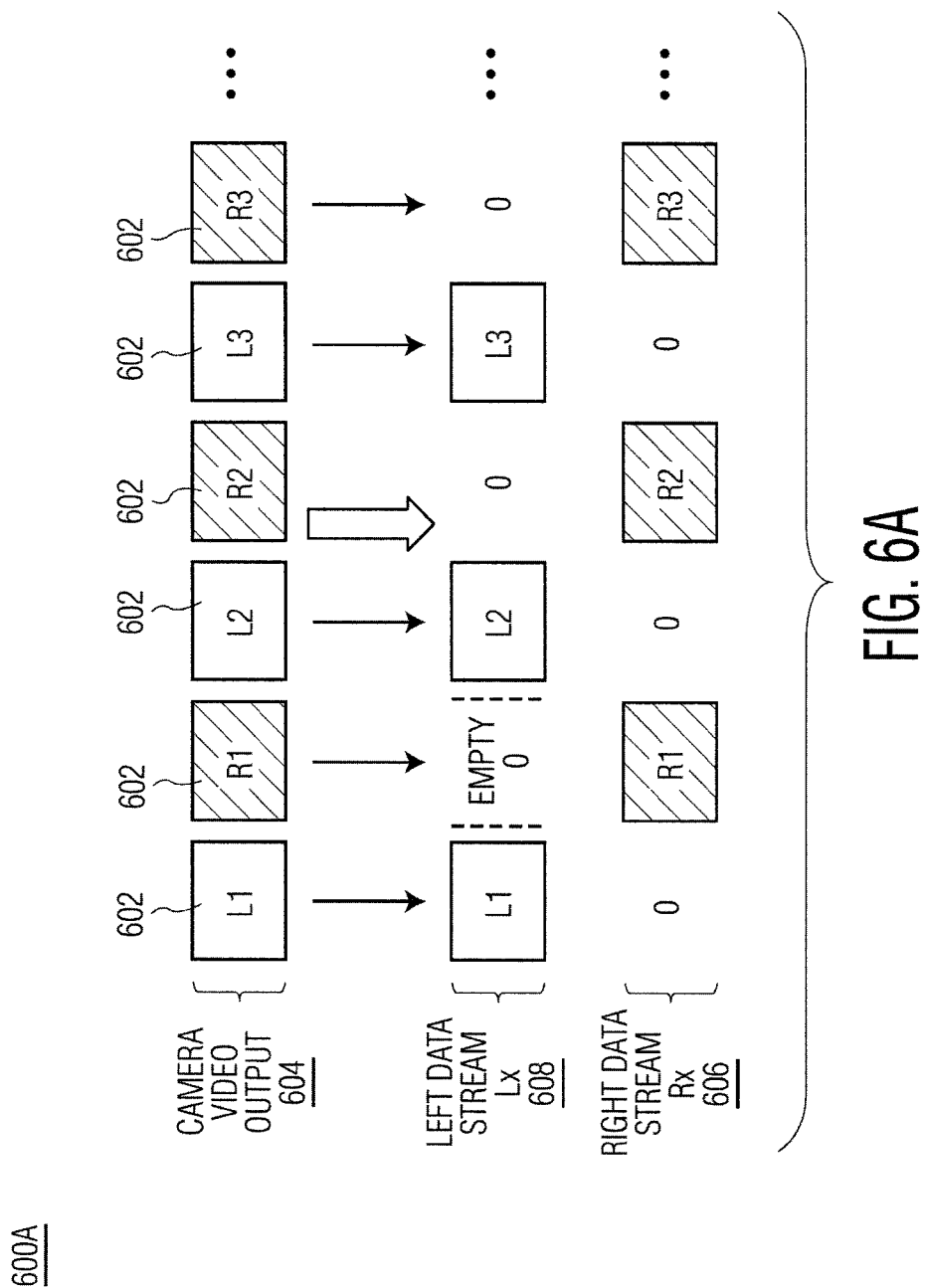

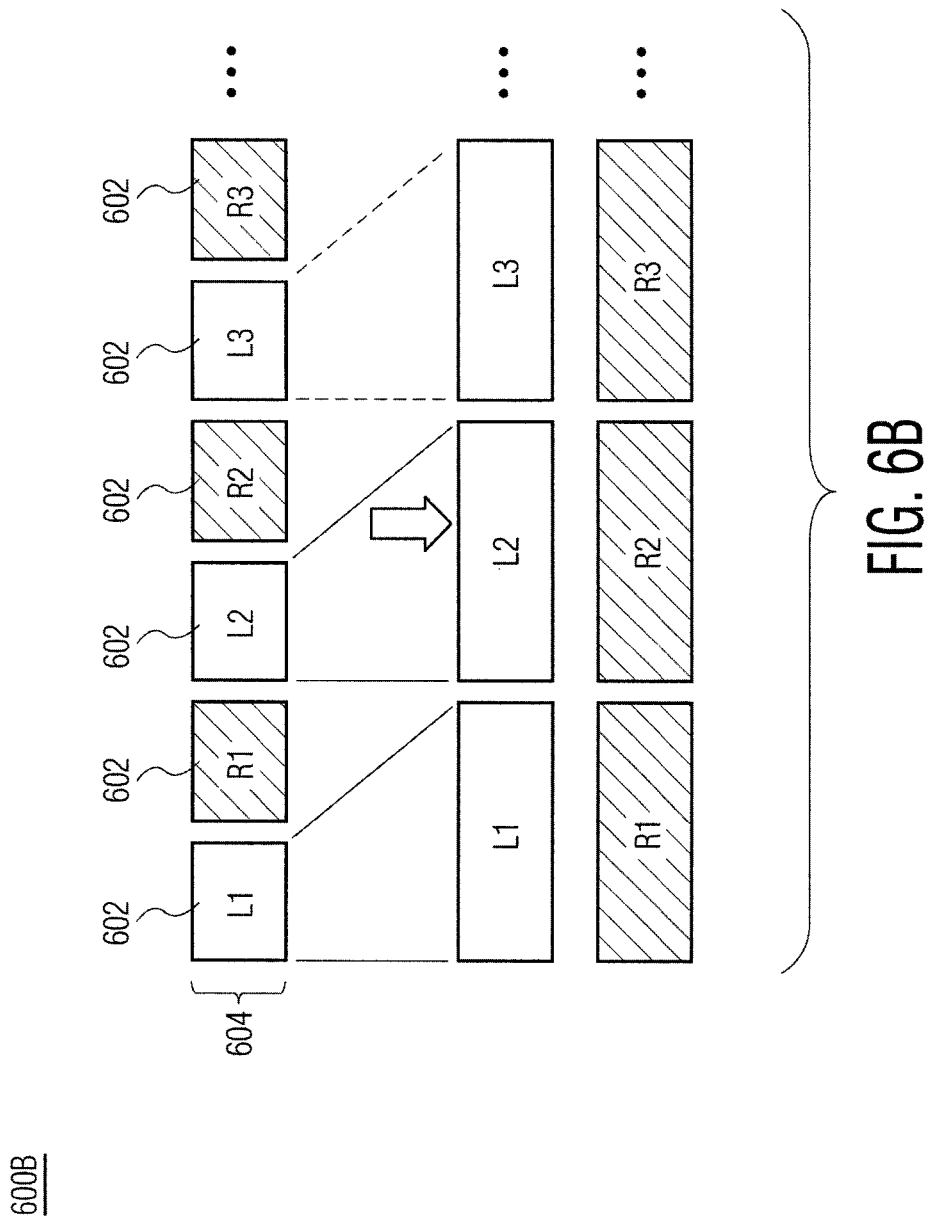

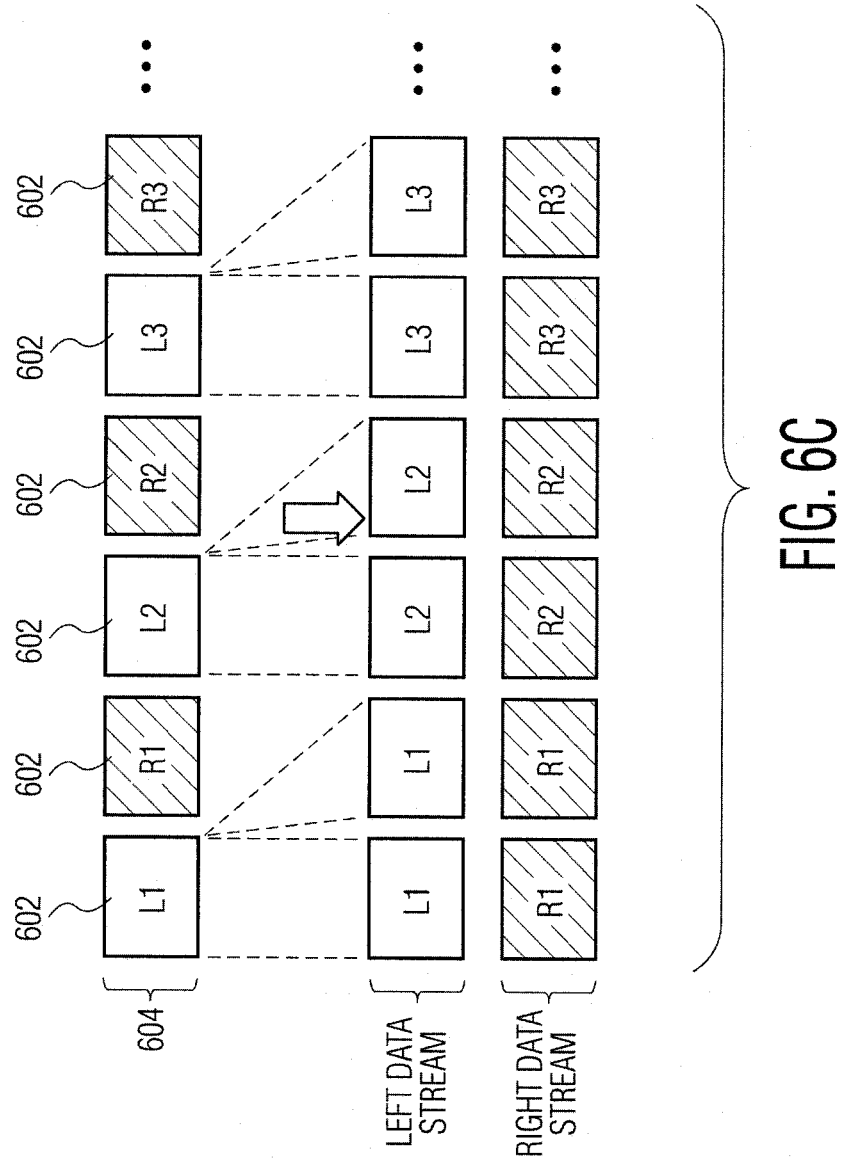

PROGRAMMABLE SPECTRAL SOURCE AND DESIGN TOOL FOR 3D IMAGING USING COMPLEMENTARY BANDPASS FILTERS

This application claims the benefits of U.S. Provisional Patent Application Ser. No. 61/539,808 filed Sep. 27, 2011, which is incorporated herein by reference in its entirety.

The invention described herein was made in the performance of work under a NASA contract, and is subject to the provisions of Public Law 96-517 (35 USC 202) in which the Contractor has elected to retain title.

Further, each of the following patents or patent applications is incorporated herein by reference in its entirety:

(1) U.S. Pat. No. 7,601,119 B2, to Shahinian, entitled "Remote Manipulator with Eyeballs," filed on Apr. 25, 2006 and issued on Oct. 13, 2009;

U.S. Patent Application Publication No. 2009/0187072 A1 to Manohara, et al., entitled "Endoscope and System and Method of Operation thereof," filed on Dec. 18, 2008, and issued as U.S. Pat. No. 8,323,182 on Dec. 4, 2012;

(3) U.S. Patent Application Publication No. 2011/0115882 A1, to Shahinian, et al., entitled "Stereo Imaging Miniature Endoscope with Single Imaging Chip and Conjugated Multi-Bandpass Filters," filed on Nov. 15, 2010; and U.S. patent application Ser. No. 13/628,896 filed on Sep. 27, 2012, and published as U.S. Patent Application Publication No. 2014/0088361, to Shahinian, et al., claiming priority to U.S. Provisional Patent Application Ser. No. 61/539,842 filed on Sep. 27, 2011, entitled "Multi-Angle Rear-Viewing Endoscope and Method of Operation Thereof."

The present system relates generally to an illumination system for medical imaging systems and, more particularly, to an illumination system for endoscopes capable of capturing stereoscopic images, and a method of operation thereof.

Minimally invasive surgery (MIS) includes surgical and other procedures which are typically less invasive than traditional open procedures such as, for example, conventional open surgery. A MIS procedure usually involves the manipulation of one or more endoscopic devices that can be inserted through an opening or incision and an endoscope or the like to observe a surgical area (or field). Unfortunately, conventional two-dimensional endoscopic viewing systems do not convey depth information of a surgical volume of interest (VOI) which may be provided by stereoscopic endoscopic (i.e., 3D) viewing systems. Accordingly, to enhance a depth-of-field of captured images of a surgical VOI, surgeons may rely upon stereoscopic endoscope imaging systems. However, conventional stereoscopic endoscopic viewing systems require bulky optical switching elements and are unsuitable use in small-diameter endoscopes such as scopes having an outer diameter of about 5 mm or less. Further, conventional techniques to produce stereoscopic images are unreliable, and difficult and costly to operate. Accordingly, the present system provides a novel, reliable, easy to operate, and inexpensive stereoscopic imaging system.

Embodiments of the present system, device(s), method, user interface, computer program, etc., (hereinafter each of which will be referred to as system unless the context indicates otherwise) described herein address problems in prior art systems. In accordance with embodiments of the present system, disclosed are systems and methods for to illuminate a subject (e.g., a volume of interest, a patient, a surgical zone, a surgical area, an area of interest, etc.) for capturing and viewing of 2-dimensional (2D) and 3-dimensional (3D) stereoscopic images.

In accordance with an aspect of the present system, there is disclosed an endoscopic illumination system for illuminating a subject for stereoscopic image capture, the illumination system comprising: a light source which outputs multi-spectral light; first and second light paths configured to transmit the multi-spectral light; a digital mirror array and/or device (DMA/DMD) which receives the multi-spectral light and directs the multi-spectral light to a selected one of the first and second light paths; a controller which controls the DMA to direct the multi-spectral light to the selected light path in accordance with a time-multiplexing scheme; and/or first and second complementary multiband bandpass filters (CMBF), the first CMBF situated in the first light path and the second CMBF situated in the second light path, wherein the first and second CMBFs filter the multi-spectral light incident thereupon to output filtered light.

The system may include an optics portion which may receive the multi-spectral light from the DMA and collimates the multi-spectral light which is to be incident on the selected first or second CMBFs. The system may further include transport optics which integrates the filtered light from the selected first or second CMBFs and transmits the filtered light along a third light path to illuminate the subject. Moreover, the system may include a camera which may capture video images of the subject and may generate corresponding video information and a synchronization signal, the video information including a plurality of left and right image frame information. Further, the system may include a synchronizer which determines a delay interval $\Delta t$ in accordance with the plurality of left and right image frame information and generates a trigger signal in accordance with the synchronization signal and the delay interval $\Delta t$ for each of the left and right image frames. Moreover, the DMA may control timing of illumination to the selected one of the first or second light paths in accordance with the trigger signal.

In accordance with yet another aspect of the present system, there is disclosed an endoscopic illumination method for illuminating a subject for stereoscopic image capture, the illumination method may be controlled by a controller having one or more processors, the illumination method comprising acts of: outputting, by a light source, multi-spectral light; selectively passing, using a digital mirror array (DMA), the multi-spectral light to a selected one of first and second light paths in accordance with a time-multiplexing scheme, the first light path having a first complementary multiband bandpass filter (CMBF) and the second light path having a second CMBF; filtering, by the selected first or second CMBF, the multi-spectral light incident thereon and outputting filtered light; and/or illuminating the subject using the filtered light.

It is also envisioned that the method may include acts of receiving the multi-spectral light passed by the DMA; and collimating the multi-spectral light which is to be incident on the selected first or second CMBFs of the optics portion. Further, the method may include the act of integrating the filtered light from the selected first or second CMBFs; and transmitting the filtered light along a third light path to illuminate the subject. It is also envisioned that the method may include acts of: capturing video images of the subject; and generating corresponding video information and a synchronization signal, the video information including a plurality of left and right image frame information, the synchronization signal corresponding to a start time of an act of capturing a left or a right image frame. Further, the method may include acts of determining a delay interval $\Delta t$ in accordance with the plurality of left and right image frame information; and generating a trigger signal in accordance with the synchronization signal and the delay interval $\Delta t$ for each of the left and right image frames.

It is also envisioned that the method may include an act of controlling timing of illumination to the selected one of the first or second light paths in accordance with the trigger signal.

In accordance with yet another aspect of the present system, there is disclosed a computer program stored on a computer readable memory medium, the computer program configured to control illumination of a subject for stereoscopic image capture, the computer program comprising: a program portion configured to: output, by a light source, multi-spectral light; selectively pass, using a digital mirror array (DMA), the multi-spectral light to a selected one of first and second light paths in accordance with a time-multiplexing scheme, the first light path having a first complementary multiband bandpass filter (CMBF) and the second light path having a second CMBF; filter, by the selected first or second CMBF, the multi-spectral light incident thereon and outputting filtered light; and illuminate the subject using the filtered light.

It is also envisioned that program portion may be configured to: receive the multi-spectral light passed by the DMA; and/or collimate the multi-spectral light which is to be incident on the selected first or second CMBFs of the optics portion. Further, the program portion may be further configured to: integrate the filtered light from the selected first or second CMBFs; and transmit the filtered light along a third light path to illuminate the subject. It is also envisioned that the program portion may be configured to: capture video images of the subject; and generate corresponding video information and a synchronization signal, the video information including a plurality of left and right image frame information, the synchronization signal corresponding to a start time of an act of capturing a left or a right image frame. Moreover, the program portion may be further configured to: determine a delay interval Δt in accordance with the plurality of left and right image frame information; and generate a trigger signal in accordance with the synchronization signal and the delay interval Δt for each of the left and right image frames. It is also envisioned that the program portion may be further configured to control timing of illumination to the selected one of the first or second light paths in accordance with the trigger signal.

In accordance with yet a further aspect of the present system, there is disclosed an endoscopic illumination system for illuminating a subject for stereoscopic image capture, the illumination system comprising: a light source which outputs multi-spectral light; a dispersive optical element which spatially separates wavelengths of the multi-spectral light; a digital mirror array (DMA) which receives the spatially separated wavelengths and passes the selected wavelengths of the spatially separated wavelengths to a light path; and/or a controller which controls the DMA to pass the selected wavelengths in accordance with a time-multiplexing scheme. Further, the dispersive optical element may include a prism or a grating.

The invention is explained in further detail, and by way of example, with reference to the accompanying drawings wherein:

FIG. 6A is a graph of frames of the video output signal in time in accordance with embodiments of the present system;

FIG. 6B is a graph illustrating the half data rate fill technique in accordance with embodiments of the present system;

FIG. 6C is a graph illustrating the half data rate fill technique in accordance with embodiments of the present system;

Figure 8:
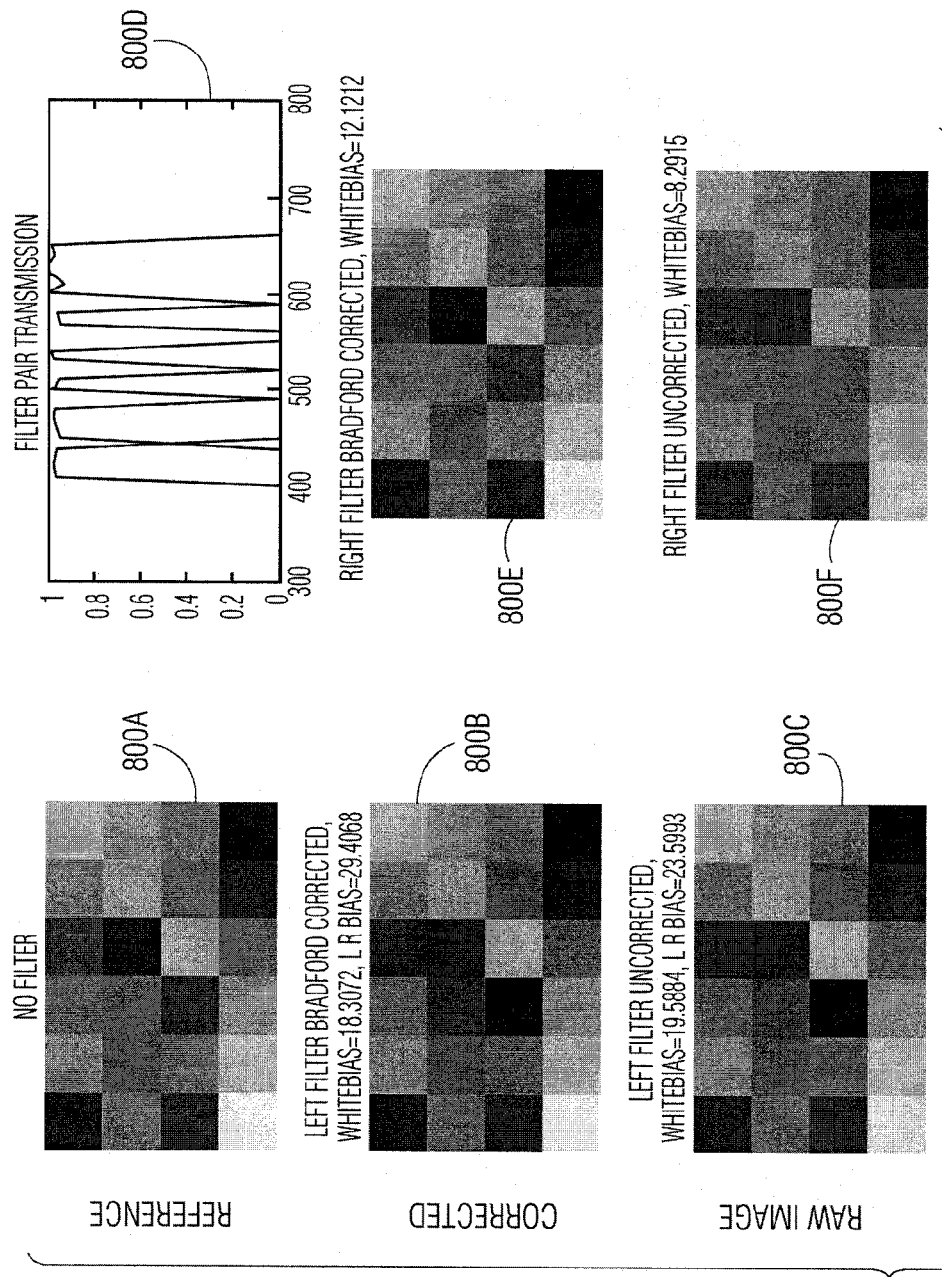
Figure 9:
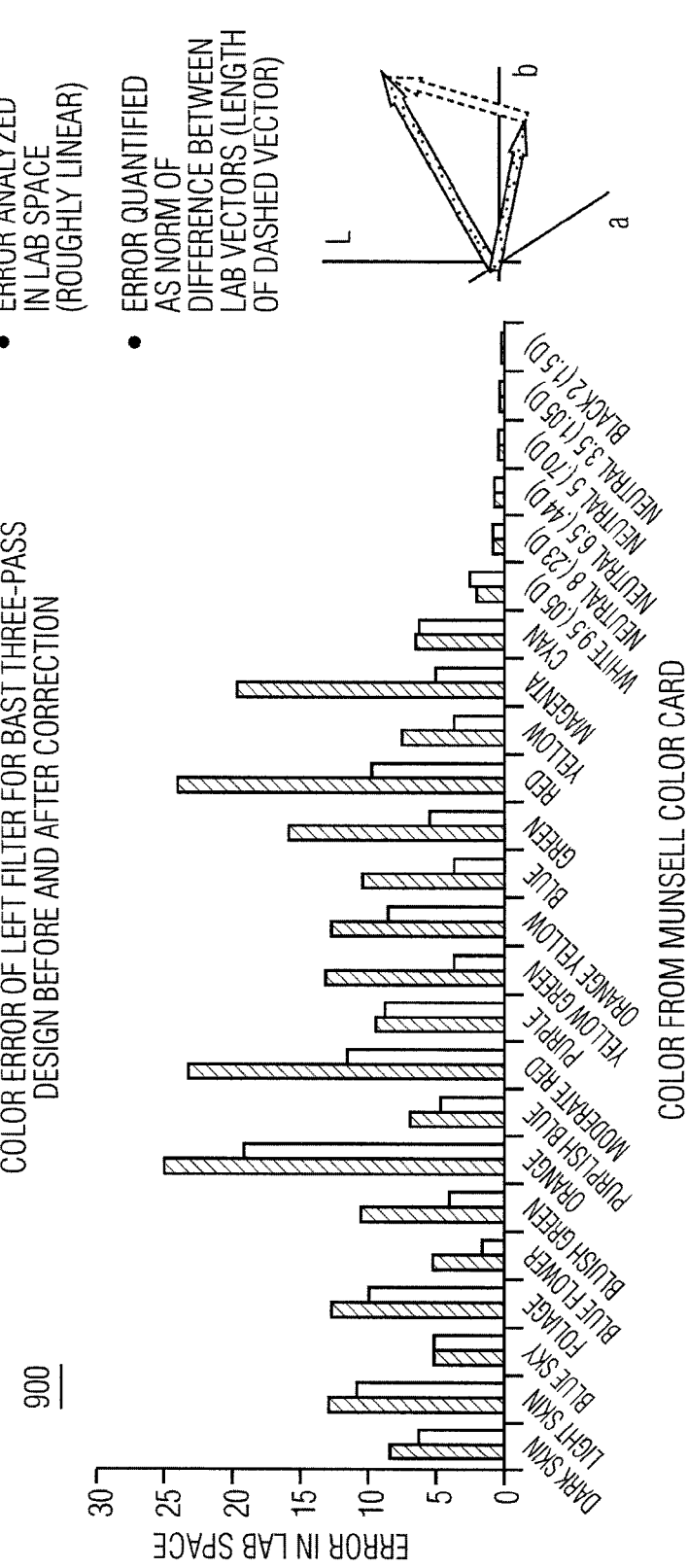
Figure 10:
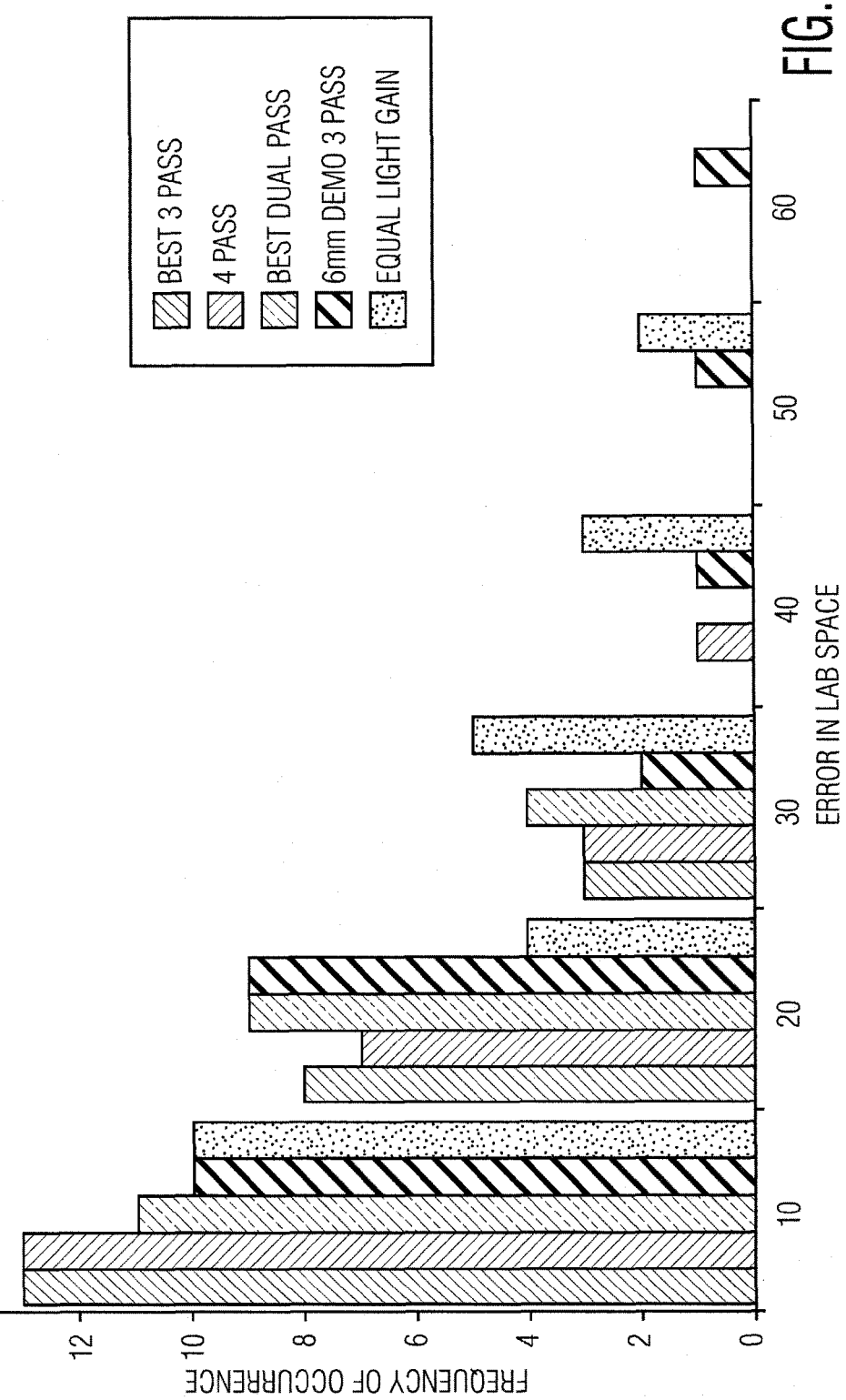
Figure 11A:
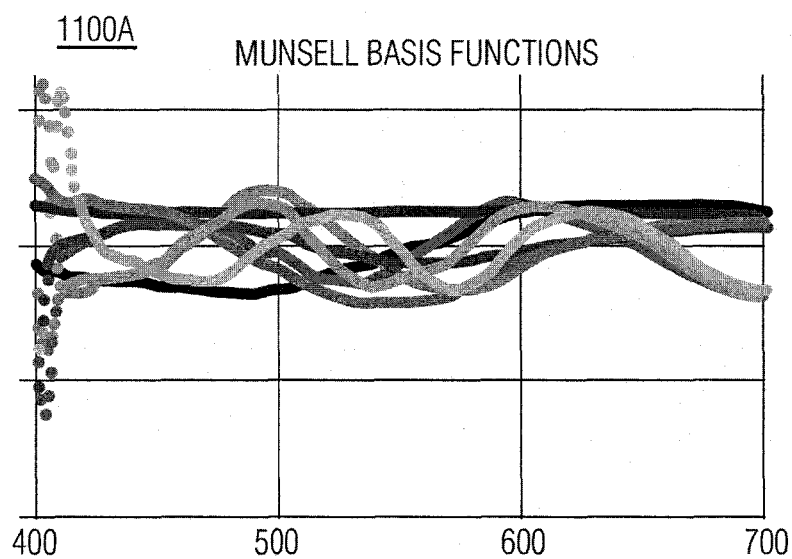
Figure 11B:
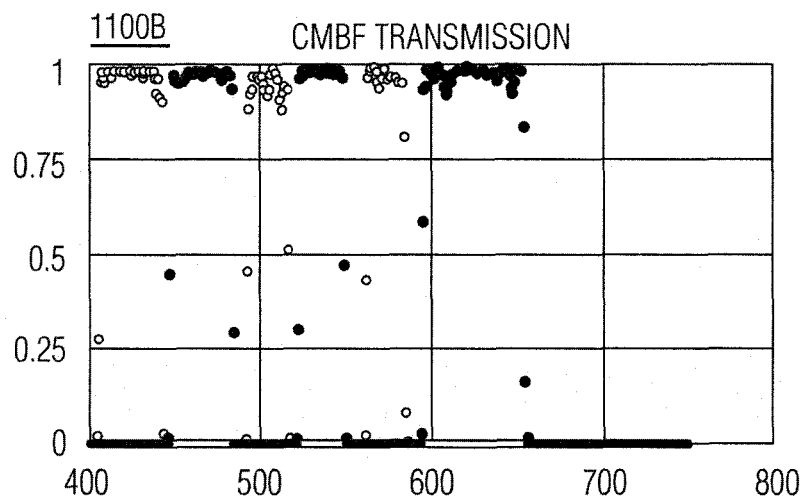
Figure 11C:
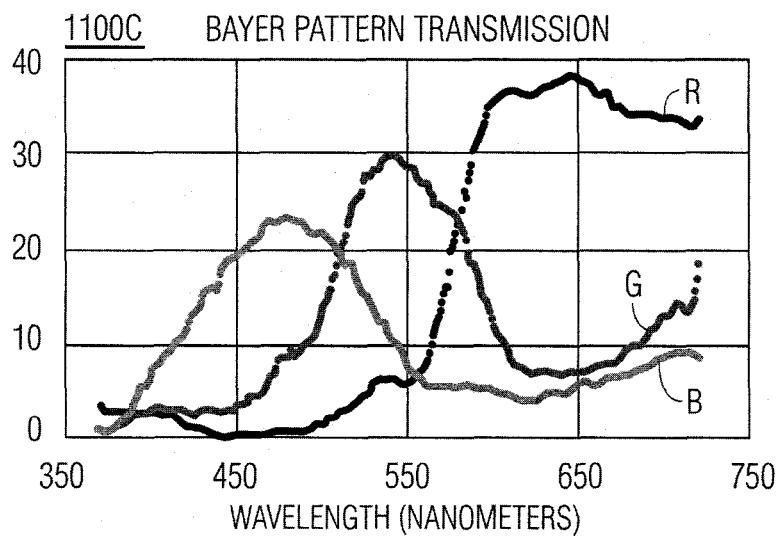
Figure 12:
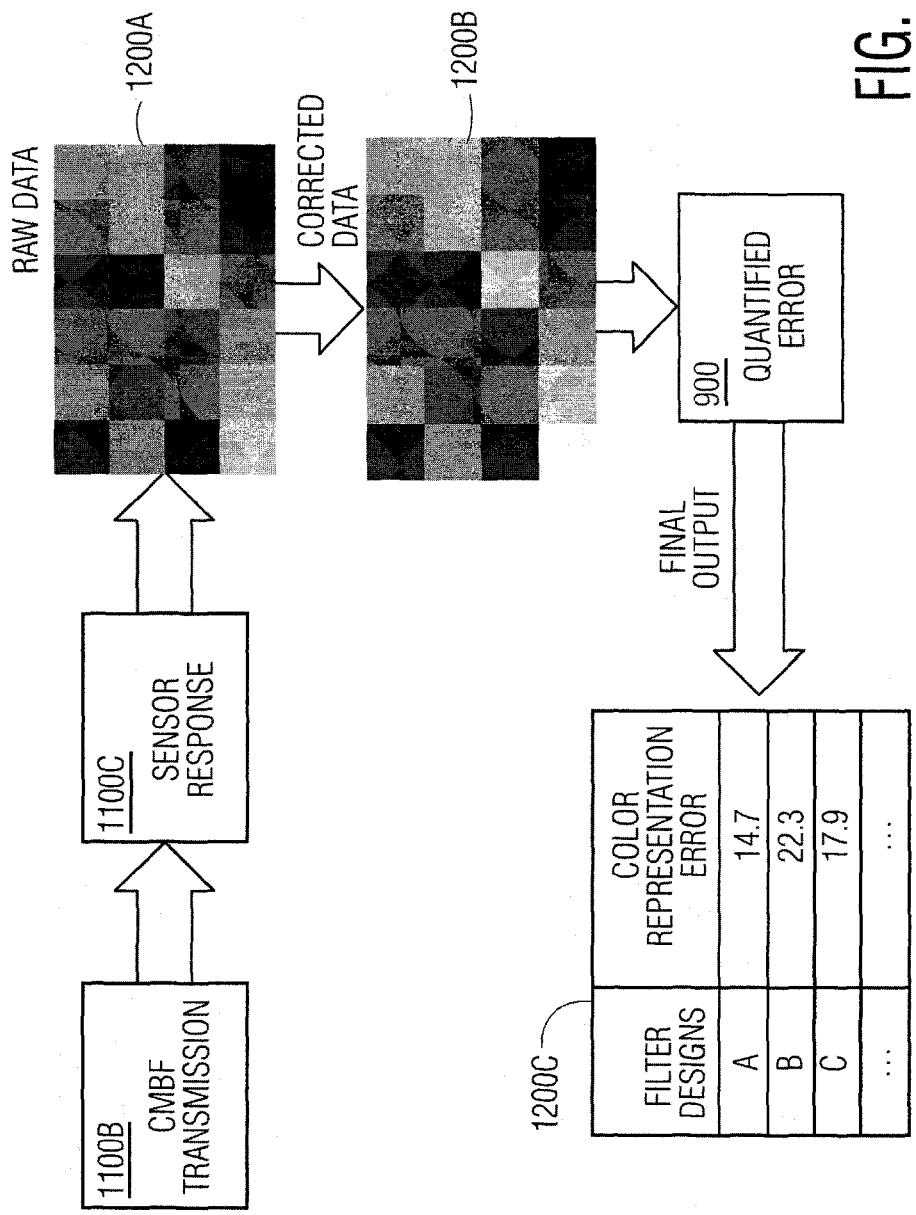
Figure 13:
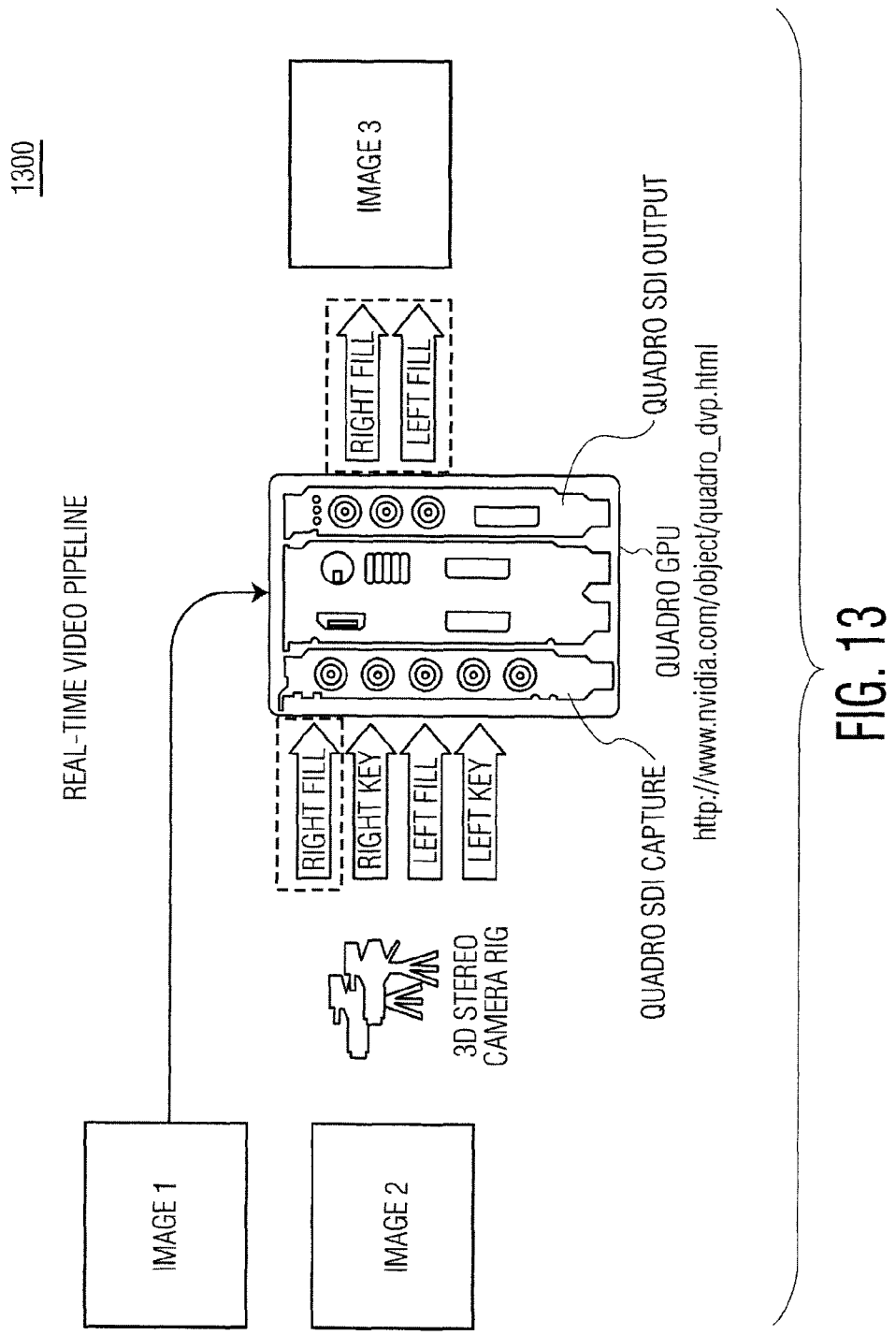
Figure 14:
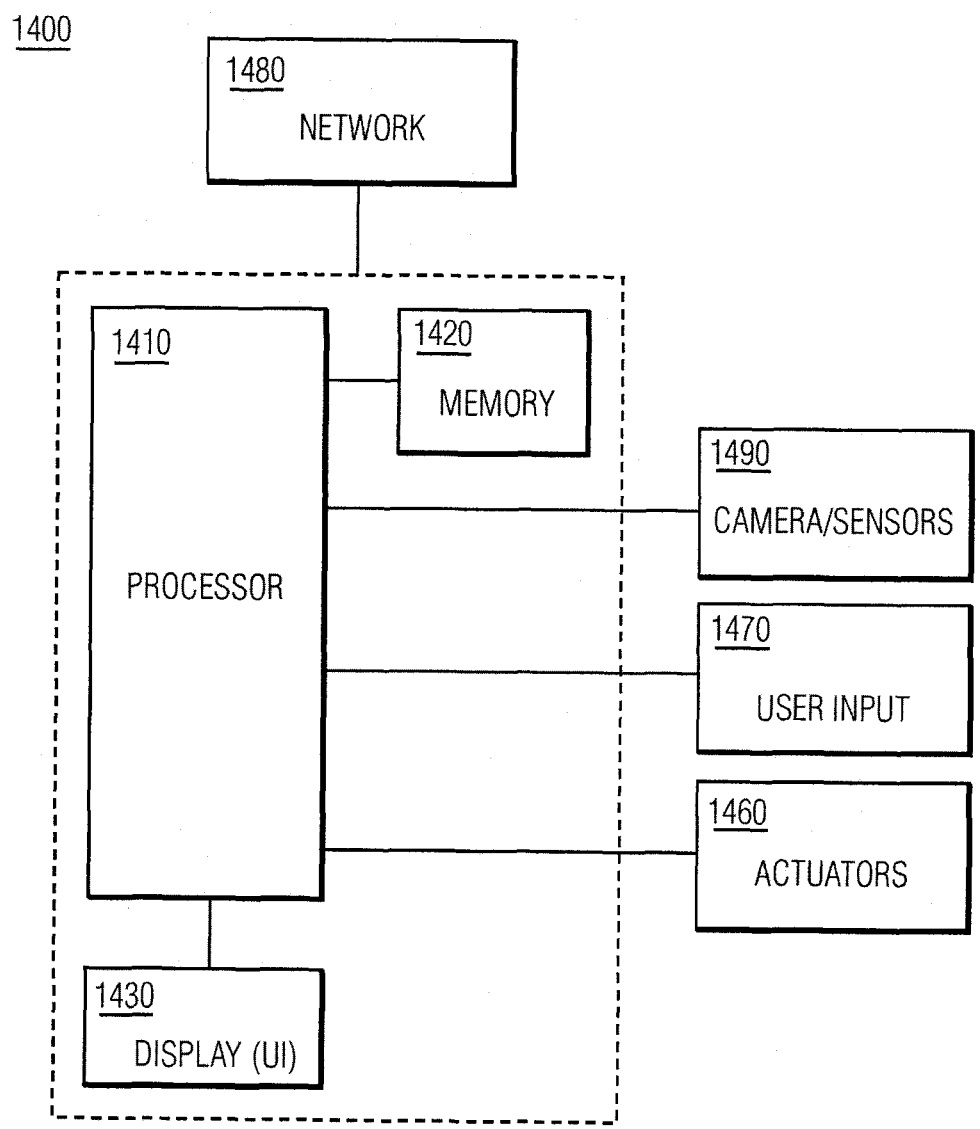

FIG. 8 includes graphs which illustrate an application of a Bradford Matrix in accordance with embodiments of the present system;

FIG. 9 shows a graph illustrating error reduction after Bradford correction in accordance with embodiments of the present system;

FIG. 10 shows a graph of a histogram of error of left filters without chromatic adaptation in accordance with embodiments of the present system;

FIGS. 11A-C show graphs of spectral curves for error correction in accordance with embodiments of the present system;

FIG. 12 shows graphs illustrating an error correction method in accordance with embodiments of the present system;

FIG. 13 shows a schematic flow diagram 1300 of an available image capture pipeline system that may be used to capture 3D images using the illumination systems of the present embodiments; and FIG. 14 shows a portion of a system (e.g., peer, server, etc.) in accordance with an embodiment of the present system.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number. Moreover, for the purpose of clarity, detailed descriptions of certain features will not be discussed when they would be apparent to those with skill in the art so as not to obscure the description of the present system.

Figure 1:
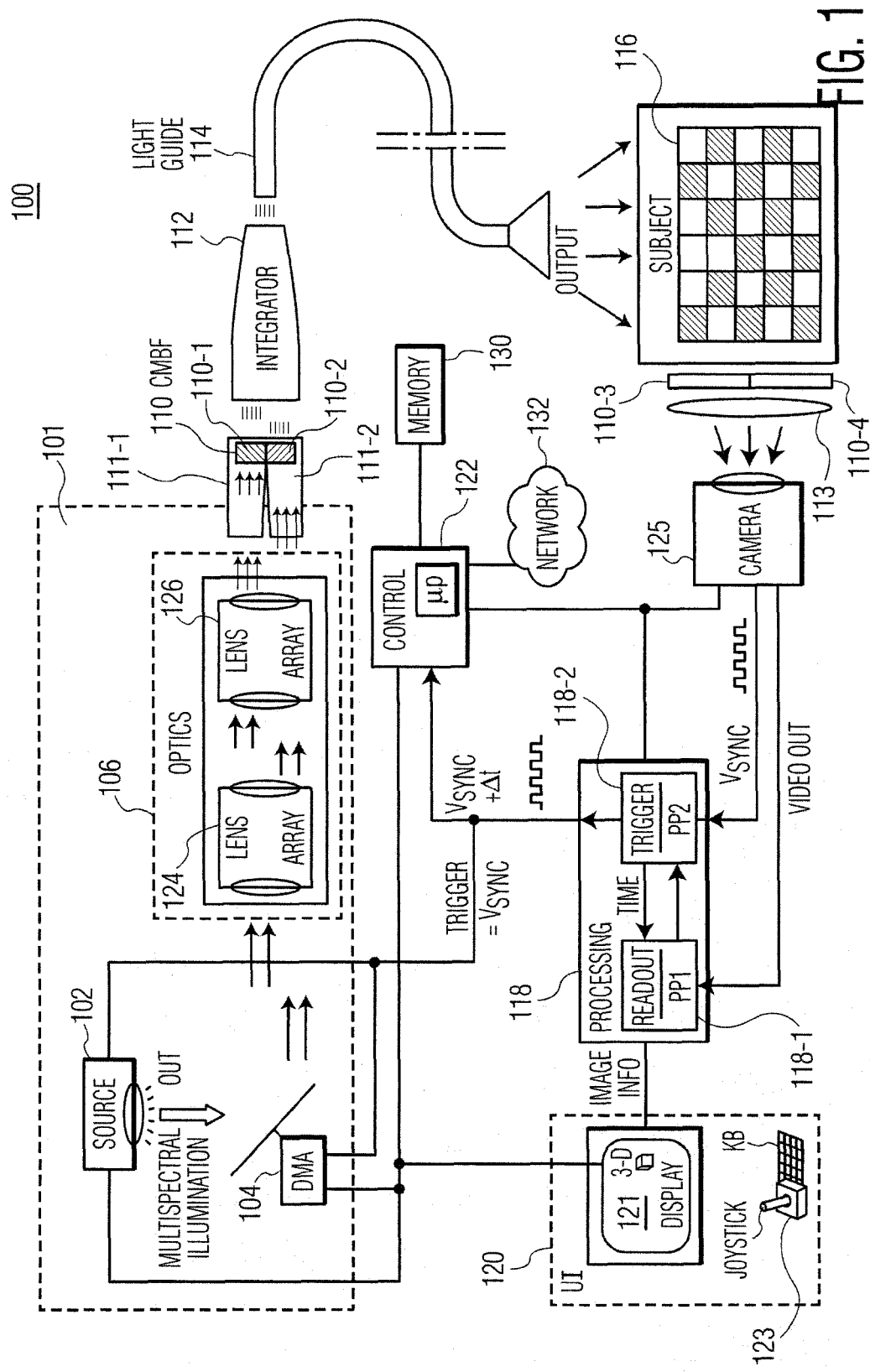
FIG. 1 is a schematic flow diagram of a portion of an endoscopic system (hereinafter system for the sake of clarity) according to embodiments of the present system.
Figure 2:
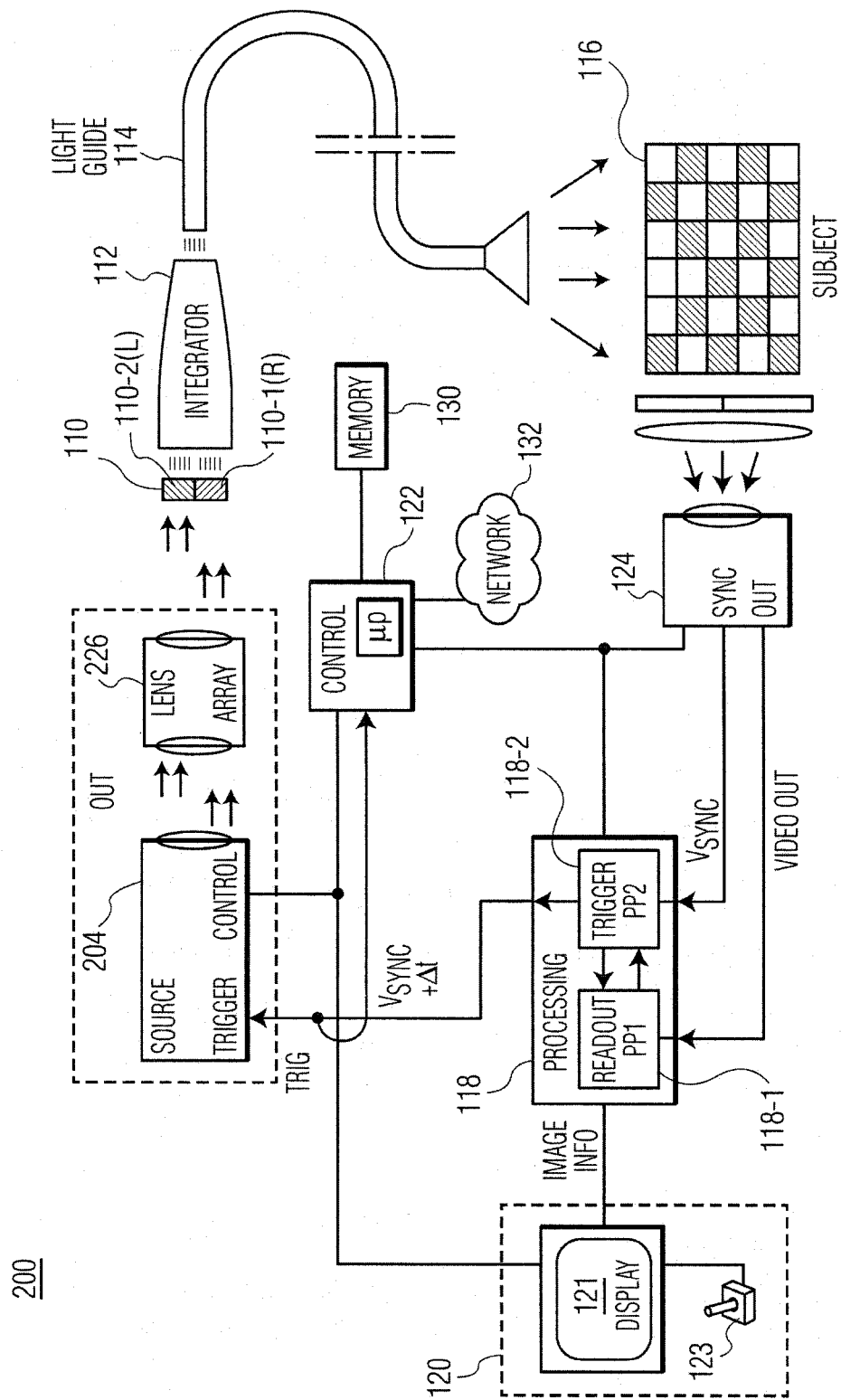
FIG. 2 is a schematic flow diagram of a portion of an endoscopic system (hereinafter system for the sake of clarity) according to embodiments of the present system.

Two methods using similar digital mirror array (DMA) technology will be described below. The first of these methods shown and described with reference to FIGS. 1 and 2 is a filter-based method which uses a spatial pattern generated by a DMA to selectively illuminate different parts of illumination complementary bandpass filters (CMBFs) of a CMBF pair matched to transmission of CMBF pair in the camera, also referred to as pupil CMBF pair. In particular, the illumination is identical to the pupil CMBF pair having identical complementary passbands shown in FIG. 4D, and further described in U.S. Patent Application Publication 2011/0115882 and U.S. Patent Application Publication No. 2014/0088361 filed on Sep. 27, 2012, and claiming priority to U.S. Provisional Patent Application Ser. No. 61/539,842. The second method is referred to as a filterless method which uses a dispersive optical element such as a prism, grating, etc. to separate the wavelengths of an input light source spatially. Then a DMA selectively passes or rejects these separate wavelengths based on the on/off state of a mirror of the DMA.

Regardless of method used, computational methods (e.g., digital signal processing (DSP)), etc., may be performed on generated signal information (e.g., video out, and sync as will be discussed below) using any suitable mathematical modeling methods and/or numerical analysis methods such as may be provided by Matlab™. For example, DSP may be performed using standard Matlab™ DSP libraries, etc.

1. Filter Based Methods

A schematic flow diagram of a portion of an endoscopic system 100 (hereinafter system for the sake of clarity) according to embodiments of the present system is shown in FIG. 1. The system 100 includes one or more of an illumination portion 101, a CMBF pair 110, an integrator 112, a light guide 114, an image capture device such as a camera 125, a processing portion 118, a controller 122, a memory 130, and a user interface (UI) 120.

Figure 4A:
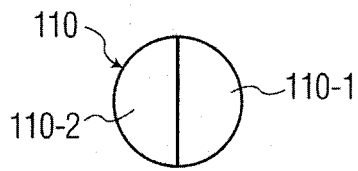
FIG. 4A is a front view of the CMBF pair in accordance with embodiments of the present system.

The CMBF pair 110 is also referred to an illumination CMBF pair (i.e., right and left CMBFs 110-1, 110-2) which is matched or identical to a pupil CMBF pair 110-3, 110-4 that receives light provided through the illumination CMBF pair and reflected from the subject or object of interest 116 for selective sequential passage by the pupil CMBF pair of right and left images toward detector optics and a detector or camera 125 having a single focal plane array (e.g., CMOS or CCD) for obtaining stereoscopic 3-D images, where the detector optics including the pupil CMBF pair and the detector or camera 125 are included in a small housing, such as a cylindrical housing having a diameter of 3 mm-5 mm. The detector optics comprises a detection lens system that includes a detection lens 113 having one un-partitioned section that covers both the right pupil CMBF 110-3 and a left pupil CMBF 110-4, for directing and/or focusing light passing through the pupil CMBFs 110-3, 110-4 onto the camera 125, such as described in U.S. 2011/0115882, and U.S. 2014/0088361, which claims priority to U.S. Provisional Patent Application Ser. No. 61/539,842. For example, the detection lens system includes optical lenses and elements that are serially connected back to back sharing a central axis and having a same diameter, such as slightly less than 4 mm, so at to fit within a 4 mm outer housing of an image capture device including the camera 125 and the detection lens system. The outer diameter of the housing may be in the range of 2-4 mm, for example. Further, for example, both the illumination CMBF pair 110-1, 110-2 and the pupil CMBF pair 110-3, 110-4 have 3 right passbands 501-1 and 3 left passbands 501-2, as shown in FIG. 4D.

The controller 122 may control the overall operation of the system 100 and may include one or more processors such as microprocessors and/or other logic devices which may be locally or remotely situated relative to each other. Further, the controller 122 may communicate via a network such as the network 132 which may include, for example, a local area network (LAN), a wide area network (WAN), a system bus, the Internet, an intranet, a proprietary network, a wireless network, a telephonic network (e.g., 3G, 4G, etc.), etc. and may send and/or receive information from, for example, distributed portions of the system such as processors, storage locations, user interfaces (UIs), etc.

The CMBF pair 110 includes first and second CMBFs 110-1 and 110-2 (generally 110-x), respectively, as will be discussed below.

The UI 120 may include a display 121 which may render information such as image information received from the processing portion 118. Additionally, the display 121 may render other information such as applications, content, menus, time, operating parameters, etc., as may be typical of a medical imaging system, for the convenience of the user. Further, the UI 120 may include user input devices such as a joystick 123, a keyboard KB, a mouse, etc., for input of commands and/or other information by a user.

The illumination portion 101 may include one or more of a light source 102, a DMA 104, and an optical portion 106. For example, the illumination portion 101 may include a Texas Instruments™ LightCommander™ lightsource including a light emitting diode (LED) type lamps. However, the embodiments of the present system are also compatible with other light sources such as xenon lamps that provide white light and are used in the medical community.

Generally, the illumination portion 101 illuminates selected CMBF 110-x (i.e., either the right CMBF 110-1 or the left CMBF 110-2, one at a time, or sequentially) of the CMBF pair with multi-spectral light using a time multiplexing scheme as will be discussed below. Further, the illumination output and/or spectrum may be controlled. In the present system, the CMBFs 110-1 and 110-2 of the CMBF pair are situated side by side on a substrate as will be discussed below with reference to FIG. 4A. Thus, the illumination portion 101 may selectively select an area to illuminate of a plurality of areas as will be discussed below. The selected area will include only a single CMBF 110-1 and 110-2 of the CMBF pair 110.

The light source 102 may, for example, include a broadband light source such as a xenon light source which may output multi-spectral light such as broadband light. However, in yet other embodiments, the light source 102 include a plurality of light emitting diodes (LED) such as red, green and blue LEDs, the combination of which may output multi-spectral light such as white light. However, in yet other embodiments, it is envisioned that other light sources may be used. However, regardless of light source type, a lighting spectrum output by the light sources should correspond with or include passbands (such as shown in FIG. 4D) of the CMBFs 110-1 and 110-2 of the CMBF pair 110. For example, if the CMBF pair 110 only passes red, green, and blue spectrums, then the light source should at least supply illumination in these spectrums. However, in yet other embodiments, it is envisioned that the light source may supply other spectrums. The light source 102 may include one or more lenses to focus (and/or otherwise control light) emitted light which is received by the DMA 104.

The DMA 104 is configured to selectively pass the light received from the illumination portion 101 to selected CMBFs 110-1 or 110-2 of the CMBF pair 110 in the present embodiment using a time multiplexing scheme under the control of the controller 122. The timing of the DMA 104 may be controlled using, for example, a trigger signal Trig. Accordingly, after receiving the trigger signal Trig, the DMA 104 may be operative to transfer light from the illumination portion 101 to the selected CMBF 110-1 or 110-2. The trigger signal Trig may be generated in accordance with one or more a feedback signals such as a Vsync and a video signal video out which may be processed to determine timing of the trigger signal Trig. As the trigger signal Trig may be constantly transmitted for each captured video frame in real time, it may include a pulse train whose timing may be controlled by the system, such as the controller 122. As each of the CMBFs 110-1 and 110-2 may be situated in corresponding light path 111-1 and 111-2, respectively, of a plurality of light paths 111-*x*, the DMA 104 may selectively pass the light received from the illumination portion 101 to selected light path 111-1 or 111-2 of a plurality of the light paths 111-*x* (via, for example, an optics portion 106) in accordance with a time-multiplexing scheme. Once light is passed to the selected light path 111-*x*, it will be incident upon and filtered by the corresponding CMBF 110-*x*. Thus, light selectively directed by the DMA 104 to the first light path 111-1 will substantially only be incident upon the first CMBF 110-1 of the plurality of CMBFs 110-*x*. Likewise, in a next time frame, light selectively directed by the DMA 104 to the second light path 111-2 will substantially only be incident upon the second CMBF 110-2 of the plurality of CMBFs 110-*x*.

The optical portion 106 may include one or more lenses and may be configured to direct, e.g., collimate and/or focus, light received from the DMA 104 and which is to be incident upon the selected CMBF 110-1 or 110-2. Accordingly, the optical portion 106 may include one or more lenses or lens arrays such as a first lens array 124 and a second lens array 126. The first lens array 124 may collimate light received from the DMA 104 and the second lens array 126 may direct and/or focus the collimated light to the selected light paths 111-*x* and be incident upon the corresponding CMBF 110-*x*, one at a time or sequentially. Accordingly, the DMA is reimaged via the one or more lenses onto the CMBF and thus allows color toggling of the Left/Right CMBFs 110-1 or 110-2.

For example, a right light provided by the light source and DMA passes through the right illumination CMBF 110-1 to illuminate the object or volume of interest, reflect therefrom towards capture optics passing through a right pupil CMBF 110-3 for focus on an entire focal plane array of a detector to form a right image. Next, a left light provided by the light source and DMA passes through the left illumination CMBF 110-2 to illuminate the object or volume of interest, reflect therefrom towards capture optics passing through a left pupil CMBF 110-4 for focus on an entire focal plane array of a detector to form a left image. The right and left images are then processed to form a 3-D stereoscopic image of the volume of interest that provides depth information and perception, for display on a rendering device such as the display 121 or any other display, such as a heads-up display, etc.

In some embodiments, the first and second lens arrays 124 and 126, respectively, may be commercially available digital single lens reflex (DSLR) type lenses such as Nikon™ AF Nikkor 50 mm f/1.8 D lenses which are configured such that the object side (e.g., lens filter side) of the lenses are adjacent to each other. Further, the optical portion 106 may be operative to collimate light which is to be incident upon the either of the CMBFs 110-*x* such that it has an normal angle of incidence (NAOI) which is less than a threshold value (e.g., at most 23-25 degrees). However, other threshold values are also envisioned.

Each of the light paths 111-*x* may include one or more optical elements such as a corresponding CMBF 110-*x*. With regard to the CMBFs 110-*x*, each CMBF 110-*x* may be configured to transmit as much RGB-spectral information as possible for rendering a color image suitable for an intended use. Accordingly, each of the CMBFs 110-*x* should have the greatest number of passbands as possible, where only 3 are shown in FIG. 4D for simplicity.

However, the staggered passbands provides for each viewpoint to skip some regions in the RGB band. As a result, the two viewpoints take different spectral images thus render two different color images relative to each other. The raw color image from each viewpoint includes red and blue color tones. However, a difference in the color tone from each viewpoint is a product of light filtering by the corresponding CMBF 110-*x*. This difference in color tone may be narrowed by including as many complementary passbands in each CMBF of a CMBF pair. Additionally, the difference in color tone may be narrowed further by applying a Chromatic Adaptation Transform (CAT) to provide color correction.

The colors imaged through the CMBFs may appear different from the objective colors. Two methods may be used to correct the colors. One method is using the CAT. For example, while human vision can perceive a white color as white under any light condition including incandescent or sunlight, a camera images the white color differently under different light condition. For example, under yellow light condition, a camera images the white color as yellow. But, CAT is applied to change the yellow light to white if the spectrum of the yellow light is known. CAT method may be used for color correction in the present camera imaging under CMBF filtered light conditions.

Additionally or alternately, colors can be corrected to appear close to the objective colors by digital imaging processing operations (DIP) performed by the image processing portion 118, e.g., by finding a transformation matrix, which transforms wrongly placed color coordinates to correct coordinates in a color space. To find the transformation matrix, DIP assigns coordinates to the CMBF-filtered and unfiltered colors and put them in matrices. Then, DIP equates the two and inverses the CMBF matrix and multiplies the CMBF matrix on both the side. This process yields a transformation matrix. Next, the transformation matrix applies to the colors imaged through the CMBFs to correct the colors.

Each CMBF 110-*x* of the CMBF pair 110 may be separate from each other or formed integrally with each other. For example, in some embodiments, the CMBFs 110-*x* may be formed on a common substrate using, for example, a stereolithography technique so as to form an integrated CMBF pair 110. However, in yet other embodiments, the CMBFs 110-*x* may be separate from each other and located adjacent to each other or located separately from each other. Thus, a CMBF pair may be distributed. In yet other embodiments, the CMBFs 110-*x* may be adjacent to each other, and attached to a common element, such as formed on a lens by coating is with up to 100 layers of material to form an interference type filter with sharp edges. This is illustrated with reference to FIG. 4A which is a front view of the CMBF pair 110 in accordance with embodiments of the present system. The first and second CMBFs 110-1 and 110-2 are adjacent to each other and exclusively occupy corresponding areas on the CMBF pair 110. The shape and size of these areas may include, for example, half-circles as shown. In yet other embodiments, other shapes and/or sizes of these areas is also envisioned.

Figure 4B:
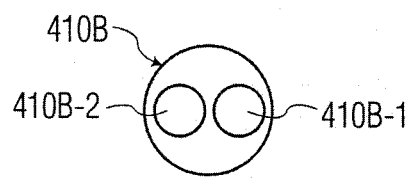
FIG. 4B is a front view of another CMBF pair in accordance with embodiments of the present system.

FIG. 4B is a front view of another CMBF pair 410B in accordance with embodiments of the present system. The CMBF pair 410B is similar to the CMBF pair 110 and includes first and second CMBFs 410B-1 and 410B-2 which may be correspondingly similar to the first and second CMBFs 410-1 and 410-2, respectively, in operation. However, unlike the first and second CMBFs 410-1 and 410-2, respectively, the first and second CMBFs 410B-1 and 410B-2, respectively, have a circular shape, where the two circle by touch or be separated from each other by any desired distance.

Figure 4C:
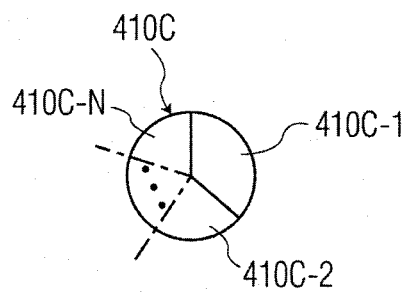
FIG. 4C illustrates a CMBF pair having N CMBFs in accordance with yet another embodiment of the present system.
Figure 4D:
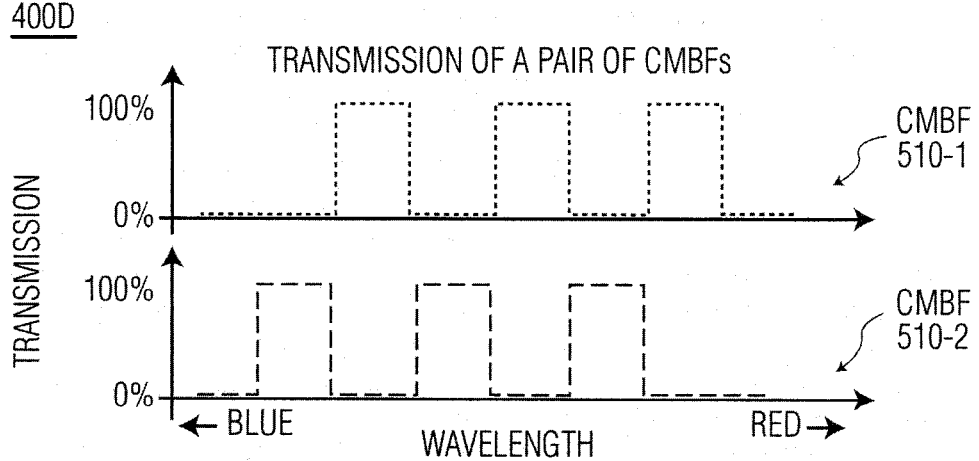
FIG. 4D is a spectral plot of light transmission by an ideal complementary triple-band bandpass CMBF in accordance with embodiments of the present system.

In yet other embodiments further numbers of CMBFs may be formed on a single substrate. For example, FIG. 4C illustrates a CMBF pair 410C having N CMBFs in accordance with yet another embodiment of the present system. Where, N is an integer greater than 2. The CMBF pair 410C includes N CMBFs 410C-1 through 410C-N each of which occupies an exclusive area and has complementary passbands.

FIG. 4D is a spectral plot 400D of light transmission by an ideal complementary triple-band bandpass CMBF in accordance with embodiments of the present system. The CMBF may include two CMBF filters such as first and second CMBF filters 410C-1 and 410C-2, respectively, which are respectively similar to the first and second CMBF filters 110-1 and 110-2, respectively, of the CMBF pair 110. Light bands passed are exclusive to each filter (e.g., 510-1 and 510-2) of a plurality of filters.

Referring back to FIG. 1, filtered light from the first and/or second CMBFs 110-1 and 110-2, respectively, is then transmitted sequentially or one at a time to the integrator 112 for transmission through to a subject 116 (e.g., an volume of interest (V01), etc. as may be typical for an endoscopic use, etc.) via, for example, a light guide 114. Light from only one of the first or second CMBFs 110-1 and 110-2, respectively, at a time is transmitted in a time-multiplexed manner. Thereafter, the camera 125 may capture images of the subject and transmit a corresponding image stream as a video output signal (e.g., including a plurality of frames each including image information) to the image processing portion 118 as video information for further processing. Further, the camera 125 may generate and transmit an output pulse such as a synchronization signal VSYNC which signals a beginning of a frame capture by the camera 125. As the frame capture is continuously preformed in time, the synchronization signal Vsync comprises a signal pulse train with each pulse corresponding with the beginning of a frame capture. The camera may include a buffer memory to store video output signals before transmission. The camera may include optics as well as the pupil CMBF pair 110-3, 110-4 which is identical to the illumination CMBF pair 110-1 and 110-2, as described in U.S. Patent Application Publication No. 2011/0115882 and U.S. Patent Application Publication No. 2014/0088361, claiming priority to U.S. Provisional Patent Application Ser. No. 61/539,842.

The image processing portion 118 may receive the Vsync signal and/or video information from the camera 125 for further processing. For example, the image processing portion 118 may include one or more processors or other logic devices which may process the video information (e.g., video out) from the camera 125 (e.g., using any suitable image processing technique and/or applications which may, for example, use digital signal processing (DSP) methods, etc.), and thereafter form corresponding image information. This image information may then be rendered on a UI of the system such as the UI 120, and/or the image information stored in a memory of the system such as the memory 130. The system may employ commercially available signal processing methods to process the image information using, for example, Matlab™ signal processing libraries or the like. Then, the image information may be analyzed to determine proper signal timing (e.g., a correct signal delay time $\Delta t$). However, other methods to determine signal timing are also envisioned.

Figure 5A:
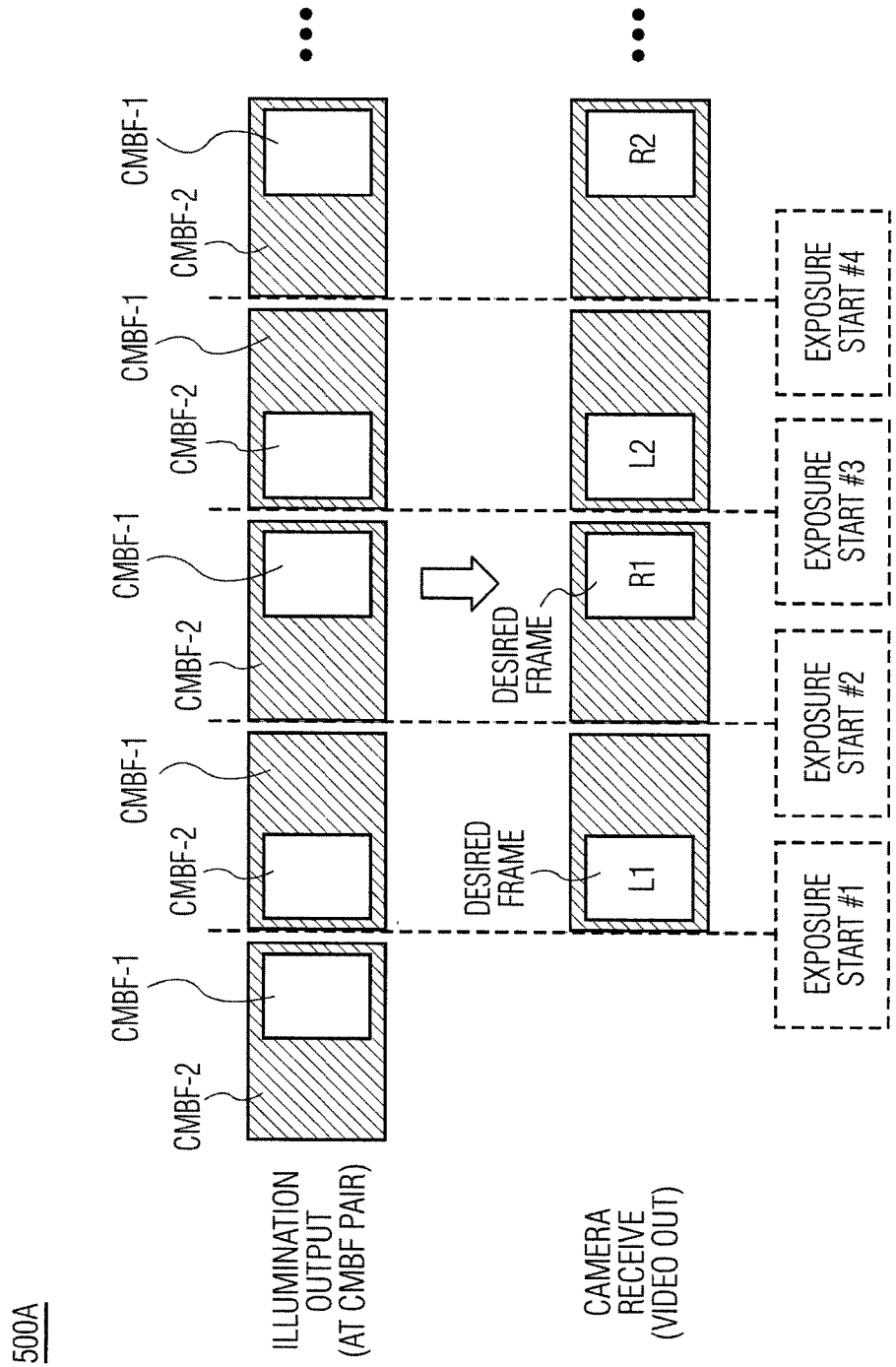
FIG. 5A is a graph illustrating synchronized output of the first and second CMBFs 110-1 and 110-2, respectively, in time in accordance with embodiments of the present system.

Further, the image processing portion 118 may determine a correct signal delay time $\Delta t$ and output a trigger signal Vsync+$\Delta t$. The trigger signal Vsync+$\Delta t$ may then be transmitted to one or more of the controller 122, the source, and/or the DMA 104 and may be used by the DMA 104 to correctly time illumination of the selected CMBF 110-x. The timing of exposure of the CMBFs 110-x is more clearly illustrated with reference to FIG. 5A which is a graph 500A illustrating synchronized output of the first and second CMBFs 110-1 and 110-2, respectively, in time in accordance with embodiments of the present system. The first and second CMBFs 110-1 and 110-2, respectively, mutually output illumination in the time domain as shown. The camera's 125 exposure is synchronized to the illumination of the CMBFs 110-x by the DMA 104 as shown. The camera 125 may then capture a plurality of frames (e.g., image frames) such as frames left 1 (L1), right 1 (R1), L2, R2, ... where the right frame refers to frames corresponding to image information of the subject 116 which were illuminated by or through the first CMBF-1, and where the left frame refers to frames corresponding to image information of the subject 116 which were illuminated by or through the second CMBF-2. The camera 125 may embed information into the frames as frame data. The frame data may include a sequence number (e.g., odd frames are left frames and even frames are right frames as identified by the system), a time stamp (the time information may identify whether a frame is a right or a left frame and a position in time of the frame relative to other frames).

Figure 5B:
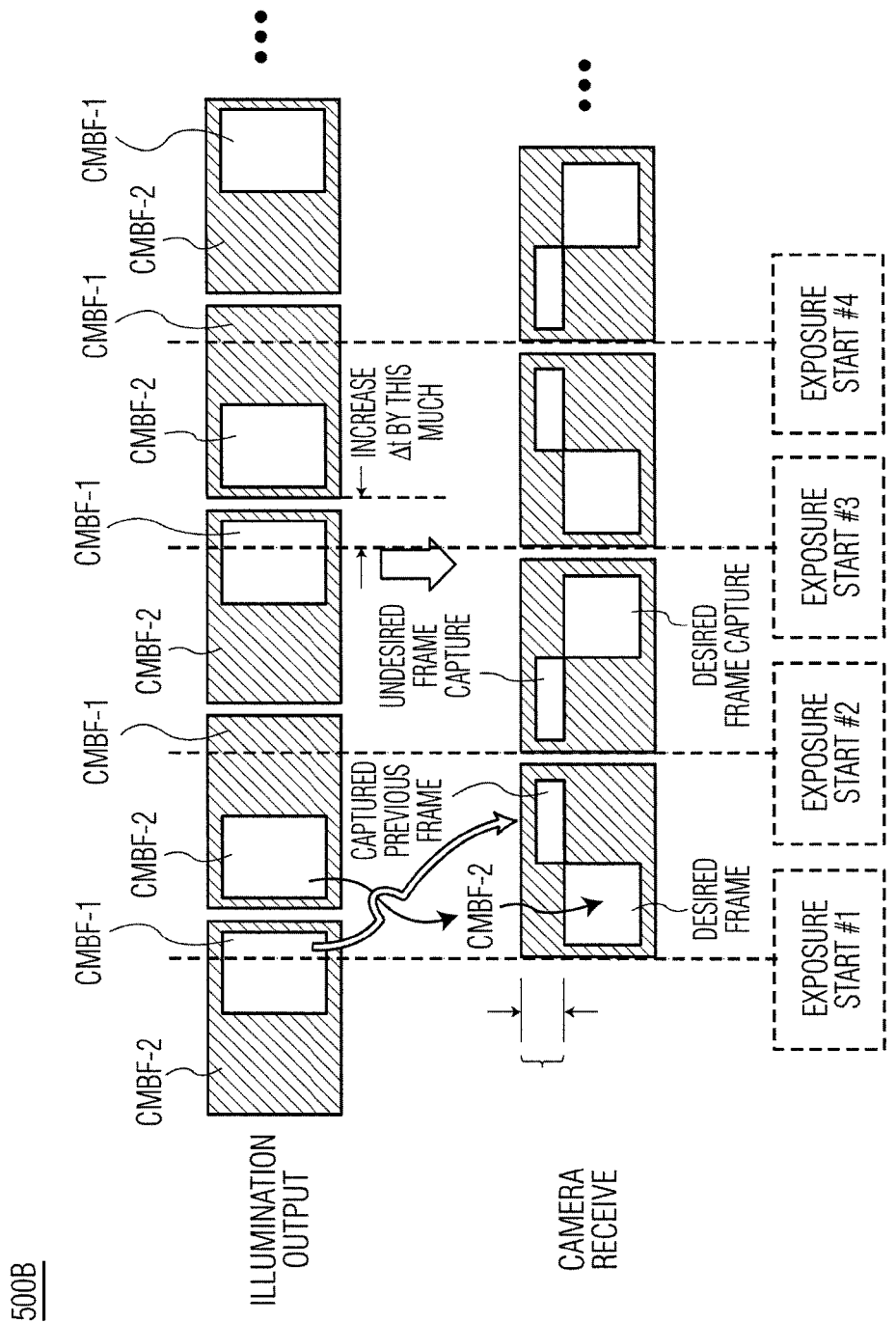
FIG. 5B is a graph illustrating unsynchronized output of the first and second CMBFs, respectively, in time in accordance with embodiments of the present system.

FIG. 5B is a graph 500B illustrating unsynchronized output of the first and second CMBFs 110-1 and 110-2, respectively, in time in accordance with embodiments of the present system. The camera's 125 exposure is not synchronized to the illumination of the CMBFs 110-x by the DMA 104 as shown. The system may employ image recognition techniques to analyze video information video out from the camera 125 (e.g., using any suitable image processing technique and/or applications which may, for example, use digital signal processing (DSP) methods, etc.), and thereafter form corresponding time delay information (e.g., increase or decrease time delay), to correct timing and form proper images similar to the images of the synchronized system.

Figure 5C:
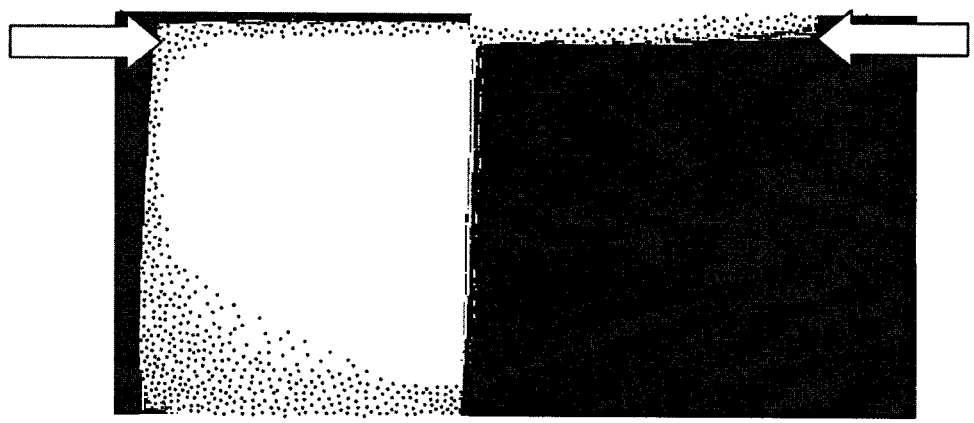
FIG. 5C is a screenshot illustrating a frame captured by the camera during unsynchronized operation.
Figure 5D:
FIG. 5D is a screenshot illustrating a frame captured by the camera during synchronized operation.

FIG. 5C is a screenshot 500C illustrating a frame captured by the camera 125 during unsynchronized operation, such as before any delay adjustment, and includes distortions at the top of the figure shown by arrows which include undesired rows that captured from previous illumination conditions. FIG. 5D is a screenshot 500D illustrating a frame captured by the camera 125 during synchronized operation, such as corrected by a proper delay, for example, determined by image recognition of images in different frames and alignment of the images for synchronization. In FIG. 5D, only illumination from a desired time period is captured, thus eliminating the undesired distortion shown by arrows in FIG. 5C.

Although feedback-based synchronization methods are described, in yet other embodiments the system may synchronize without using a feedback based signal. For example, the DMA 104 may transmit a signal (e.g., a pattern, a color, etc.) which the camera may use to synchronize with the DMA 104.

Referring back to FIG. 1, in accordance with embodiments, of the present system, the image processing portion 118 may include first and second processing portions PP1 (readout) and PP2 (trigger), respectively. Each of these processing portions PP1 and PP2 may have microcontroller such as an Arduino™ microcontroller with a high-precision clock and operate in accordance with operating instructions of embodiments of the present system so as to perform operations in accordance with routines and/or methods of embodiments of the present system. The second processing portion PP2 may be referred to as a trigger portion (as it generates and transmits the trigger signal (e.g., Vsync+Δt) and may receive the Vsync signal and/or the timing information from the camera 125. The first processing portion (PP1) may process captured image (e.g., see, FIGS. 5A and 5B), and results of the processing may then be used to control delay of the trigger signal. As the Vsync signal is generated after exposure (e.g., by the camera for a captured image frame) has started, a signal delay time Δt may be determined and added to the Vsync so as to properly control timing of the trigger signal.

Once the DMA 104 and the camera 125 are synchronized, the illumination and image capture may be considered to be synchronized.

A schematic flow diagram of a portion of an endoscopic system 200 (hereinafter system for the sake of clarity) according to embodiments of the present system is shown in FIG. 2. The system 200 is essentially similar to the system 100 shown in FIG. 2. However, rather than using the source 101 having a lens array 126, an integrated source 201 is coupled to a lens array 226. The source 226 includes a commercially available light projector (e.g., a DLP projector) such as available from DLP™ LightCommander™ from Texas Instruments, and is coupled to the lens array 226 which is similar to the lens array 126. As the combination of the source 201 and the lens array 226 includes similar inputs (e.g., trigger and control) and operates similarly to the source 101, a further discussion thereof will not be provided for the sake of brevity. The light projector may receive a control signal (control) from the controller and/or video processor) and may control an output spectrum and/or intensity accordingly. The control signal may be generated in accordance with feedback information obtained from one or more sensors and/or from analysis of the video output of the camera 125.

2. Filterless Methods

Figure 3:
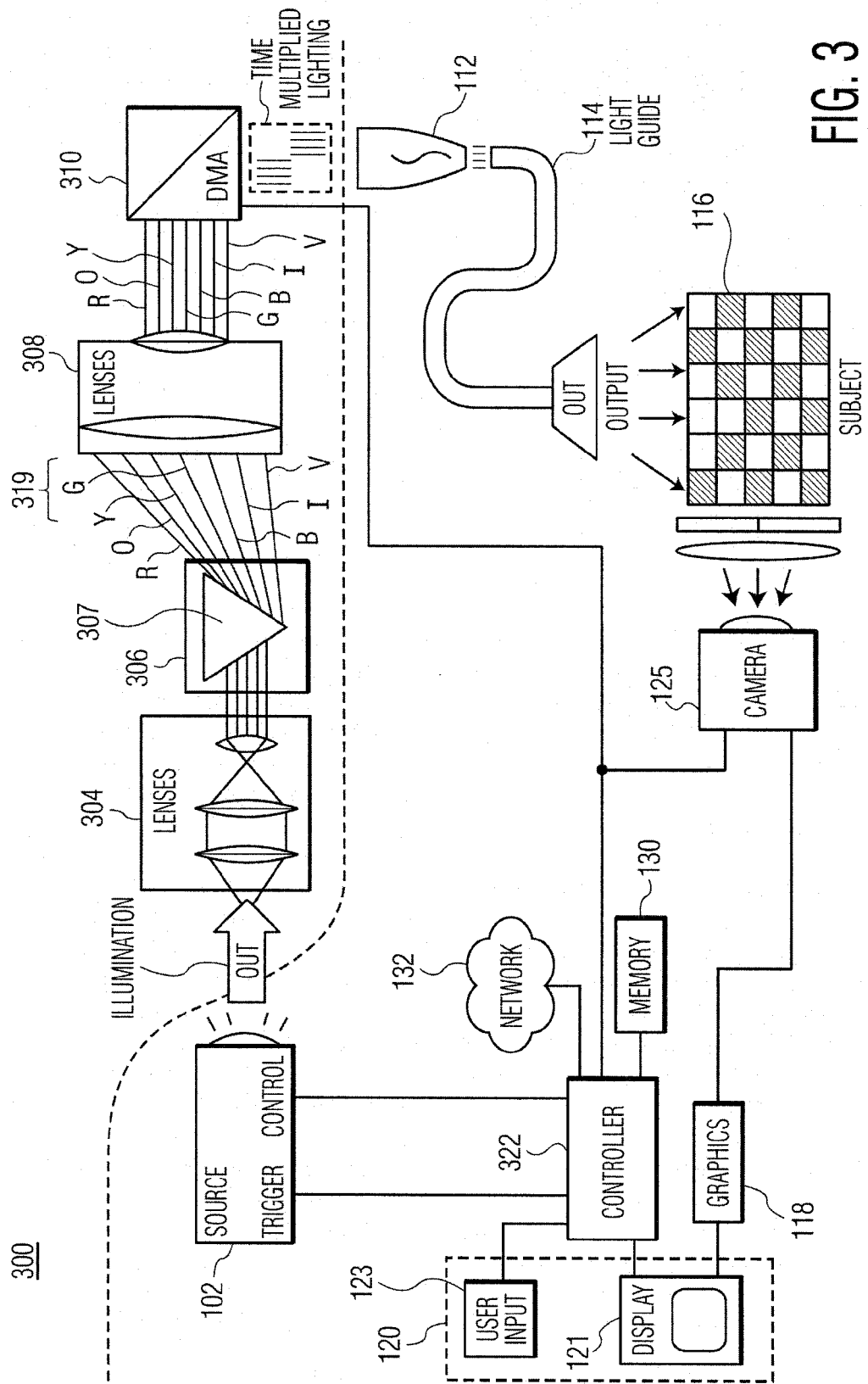
FIG. 3 is a schematic flow diagram of a portion of an endoscopic system (hereinafter system for the sake of clarity) using a filterless method according to embodiments of the present system.

A schematic flow diagram of a portion of an endoscopic system 300 (hereinafter system for the sake of clarity) using a filterless method according to embodiments of the present system is shown in FIG. 3. The system 300 includes one or more of an illumination portion including a light source 102, a first optics portion 304, a dispersive optics 306, a second optics portion 308, a DMA 310, an integrator 112 also referred to as a integrating rod or a homogenizing rod, and a light guide 114. The source 102 may output multi-spectral light such as broadband light which is input to the first optics portion 304 which collimates, focuses and directs the broadband light upon a prism 307 of the dispersive optics 306. The system 300 may be similar to the system 100 accordingly, similar numerals have been used to describe the same or similar portions and detailed descriptions of these portions will not be given for the sake of clarity. However unlike the system 100, the system 300 does not employ the use of filters, such as the CMBFs of system 100. Rather, the system 300 employs the user of the dispersive optics 306 (e.g., a dispersive optical element) such as a prism 307, grating, etc., to separate the wavelengths of input light (e.g., the broadband light) spatially to form spatially separated illumination. The spatially separated illumination (e.g., having a spread illumination spectrum as shown at 319) is then focused by the second optics portion 308 which images the spatially-dispersed illumination upon the DMA 310. Then, the DMA 310, under the control of the controller 122, selectively passes a desired spectrum of light (of a plurality of spectrums) from the spatially separated illumination to integrator 112 for transmission to, and illumination of, the subject 116. The integrating rod 112 uses total internal reflection to homogenize any non-uniform light.

As methods used to capture video images of the subject 116, image processing (e.g., DSP), timing, etc., may be performed similarly to the methods used with respect to the description of the systems shown and described with respect to FIGS. 1 and 2. Illustratively, the DMA may be configured to operate for hyperspectral imaging and/or CMBF Stereo-imaging. For example, taking the ROYGBIV of the diagram as a starting point, assume the DMA has 7 rows which pass light as follows: Row 1 passes R; Row 2 passes O; Row 3 passes Y; Row 4 passes G; Row 5 passes B; Row 6 passes I; and Row 7 passes V. For hyperspectral imaging: turn rows on sequentially to measure a 7-color (ROYGBIV) image of the scene instead of traditional 3 color (RGB). This can be extended to an N-color image where N is the number of addressable rows of the DMA. For CMBF Stereo-imaging: further CMBF filters 110-3 and 110-4 are used, also referred to as pupil CMBs filters 110-3, 110-4. Assuming the first or right CMBF 110-3 passes (R Y B V) and the second or left CMBF 110-4 passes (O G I), then a time series would be alternating frames of (1, 3, 5, 7) and (2, 4, 6).

Image Reconstruction

Figure 6D:
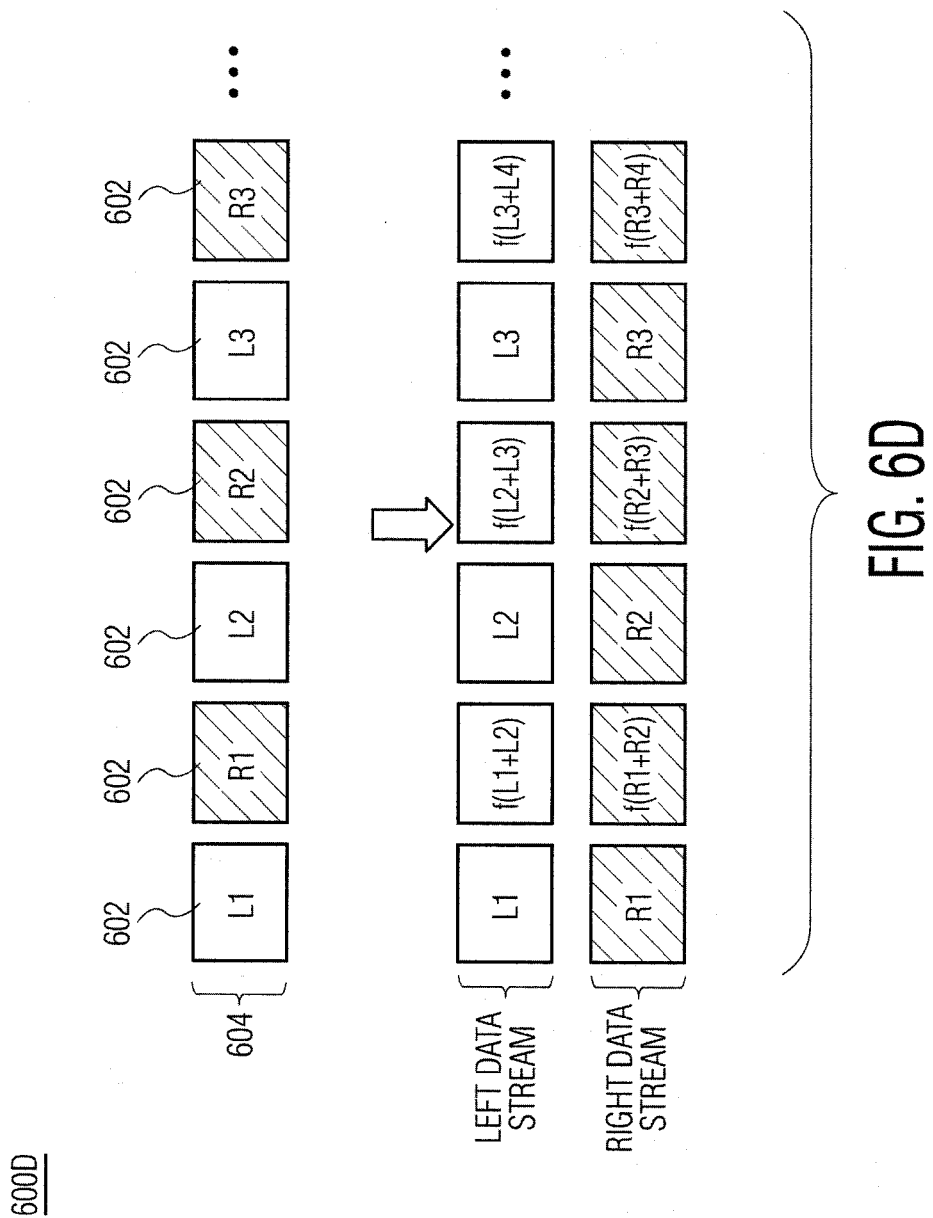
FIG. 6D is a graph 600D illustrating the interpolation technique in accordance with embodiments of the present system.

Referring back to FIG. 1, an image processor such as a video graphics processor (e.g., the PP1) may process frames of the video output signal from the camera 125 and reconstruct corresponding stereoscopic images captured by the camera 125. In accordance with a first method, the video output signal containing the left and right frames may be demultiplexed and thereafter rendered on the display 121. Accordingly, the image processor may obtain frame information identifying a frame, such as a sequence number a time stamp, etc., for each frame of a plurality of frames from the video output information. Thereafter, the image processor may interleave right and left frames together. This process is shown in FIG. 6A which is a graph 600A of frames 602 of the video output signal in time in accordance with embodiments of the present system. The right (Rx) and left (Lx) frames from the video output signal output by the camera 125 are shown in the top row 604 and may be referred to as an input data stream. The video processor then separates these frames into a right data stream 606 and a left data stream 608 each having a plurality of right or left frames, respectively. With reference to frames L1, L2, and L3 in the left data stream 608, spaces between these frames may be referred to as empty spaces (Ø) and may be filled in by the image processor. The image processor may now fill in empty spaces between adjacent frames (e.g., L1 and L2, L2 and L3, . . . ; R1 and R2, R2 and R3, . . . ) using one or more filling techniques in accordance with embodiments of the present system. These fill techniques may include, for example: (a) a half data rate fill technique; (b) a double write frame technique; and (c) an interpolation technique. These techniques will be explained with reference to FIGS. 6B-6D. In each of these figures, the input data stream is assumed to be the same.

With regard to the half data rate fill technique, a data rate of the video output stream is halved by the image processor thus, for example, if the video output is a 1080p60 data stream, the image processor would convert this data stream to a 1080p30 data stream, and thus, effectively fill in the empty spaces in the left and right data streams. FIG. 6B is a graph 600B illustrating the half data rate fill technique in accordance with embodiments of the present system.

With regard to the double write frame fill technique, in this technique each frame of the input data steam is repeated to fill an adjacent empty space. For example, each right and left frame is repeated so as to fill in the empty spaces in the left and right data streams (c f. FIGS. 6A and 6C). This is better illustrated with reference to FIG. 6C which is a graph 600C illustrating the double data rate fill technique in accordance with embodiments of the present system.

With regard to the interpolation technique, in this technique adjacent frames of each frame of the corresponding right or left input data steam are used to interpolate and fill empty space between these adjacent frames in the corresponding right or left data stream. This is better illustrated with reference to FIG. 6D, which is a graph 600D illustrating the interpolation technique in accordance with embodiments of the present system.

Illumination Control

Referring once again to FIG. 1, the camera may capture video images of the subject 116 (e.g., an object of interest) which is illuminated in accordance with embodiments of the present system. The illumination of the subject 116 may be controlled so as to properly illuminate the subject 116. Accordingly, the video information may be tagged with illumination spectrum information that is used to correct the raw image data. For example, a measured value of a light sensor output is monitored and, if the illumination is determined to be less than a threshold illumination value, the process may control the source 102 to increase illumination output. Conversely, if the illumination is determined to be greater than the threshold illumination value, the process may control the source 102 to decrease illumination output. Lastly, if the illumination is determined to be equal to (or substantially equal to) the threshold illumination value, the process may control the source 102 to hold the current the illumination output. For example, a measured value of a light sensor output is monitored. If the average value is below a first predetermined value (e.g., 10% of full scale), the output of the light source is increased. If the average value is above a second predetermined (e.g., 90% of full scale), then the output of the light source is decreased. This is to avoid underexposure and overexposure in photography terms.

The tagging of the video information with illumination information may be performed by the first processing portion PP1 that may read a current state of the illumination of the received video information. Two processing portions are used to avoid switching instability which may be caused by latency of a computer-processing board connection(s). Accordingly, the first processing portion PP1 may operate at a slow switching speed, such as 25 MHz, while the second processing portion PP2 may operate at a native clock speed, such as 16 MHz. However, in yet other embodiments, a single processor may be employed.

However, in yet other embodiments, an image processor such as an Nvidia™ Quadro™ SDI, or a field-programmable gate array (FPGA) may process the video information and form corresponding image information and/or determine timing of the system.

Color Control

In accordance with embodiments of the present system, the image processor may apply a standard or user defined color space conversion matrix to the video output stream, or may load an identity matrix and leave the color space unaltered, such as using a Chromatic Adaptation Transform (CAT), and/or digital imaging processing operations (DIP) to find a transformation matrix, to provide color correction as described above. A processor of the image processing portion 118 may carry out DIP operations to find the transformation matrix, such as by assigning coordinates to the CMBF-filtered and unfiltered colors and putting them in matrices. Then, DIP equates the two and inverses the CMBF matrix and multiplies the CMBF matrix on both the side.

Image Processing

The digital image processing operations (DIP) include manipulating images to gain any kind of useful information. Digital image processing may include operations that assign coordinates to individual elements in an image so that mathematics can be applied to extract useful information. For example, DIP can count many beans in the image, can detect a certain shape, or can calculate a speed of a moving object, etc.

In yet other embodiments of the present system, there is disclosed a design tool which simulates the all parts of the optical system and may determine characteristics of illumination sources (e.g., output spectrum, lumens, etc.) and/or CMBF filters (e.g. passbands, layers, etc.). The design tool may include a process which starts by using measured or simulated illumination spectrum from a light source. This spectrum is then passed through a hypothetical filter transmission spectrum. The resultant light is then used to calculate what a standard color checker chart (Munsell) would look like under the hypothetical illumination. This is then passed through the measured camera imager spectral response to determine the RAW values of the image. Then a color correction algorithm is employ to map the measured values as closely to the true values of the color checker chart. Finally, standard International Commission on Illumination (CIE) color accuracy metrics are computed to determine the error in 'Lab' or 'Luv' color space to determine the overall performance of the system, where 'L' is the lightness dimension and 'a', 'b', 'u', 'v' are color component dimensions. While there are other color spaces, the unique characteristic about Lab color space is that the space is flat, "perceptually uniform." Perceptually uniform means that a change of the same amount in a color value should produce a change of about the same visual importance. In this space, the color difference between two colors is simply a geodesic difference between two points in the color space, $\sqrt{x^2+y^2+z^2}$ or $\sqrt{L^2+a^2+b^2}$, where 'sqrt' is a square root operation.

These error values are computed for all colors on the chart, and the results from these simulations are compared afterwards. These values can be used to find the filter transmission that has the best overall performance. This data is used in specify the filter transmission to vendors. When vendors return their best estimate of their filter transmission, then it is verified that the performance has not been significantly degraded before moving forward on custom filter fabrication. Additionally, under fixed optical conditions, the relative performance of different color correction techniques is evaluated and the algorithm is selected that has the best performance within the system constraints of computing power and sensor noise.

Image Exposure Timing

When a frame (e.g., see, L1, L2, R1, R2, ... etc.) is captured, it is read row-by-row with a gap in exposure times (between each row) given by $\Delta t_{row}$ as defined in equation 1 below:

$$\Delta t_{row} = t_{frame}/N_{rows} = 1/30 \text{ sec}/400 = 83.3 \text{ }\mu\text{sec} \qquad \text{Eq. (1)}$$

where $t_{frame}$ is an exposure time for a corresponding frame (1/30 sec in the present example) and $N_{rows}$ is a number of rows in the frame (400 in the present example, although other number of rows such as 1080 rows are also envisioned). Accordingly, if each row has an exposure time $t_{exp}$, a timing diagram for frames having N rows would look like that shown in Table 1 below.

TABLE 1

| Row | Start Time | End Time |
|---|---|---|
| 0 | 0 | $t_{exp}$ |
| 1 | $t_{row}$ | $t_{exp} + t_{row}$ |
| 2 | $2t_{row}$ | $t_{exp} + 2t_{row}$ |
| ... | ... | |
| N | $Nt_{row}$ | $t_{exp} + Nt_{row}$ |

If flat illumination is assumed, i.e., the magnitude of illumination is constant in time, even if the system is switched from one illumination condition to another arbitrarily fast (e.g., by the DMA), some of the rows of a previous frame may be exposed during the readout of the first rows of the current frame. The rows may receive undesirable light for times $\{t_{row}, 2t_{row}, \ldots, t_{row}(()-1)\}$. This may manifest itself as crosstalk, where part of a left image frame appears in the right image frame or vice versa (e.g., see, FIG. 5B). Even when perfectly synchronized, there may be a limit on the crosstalk C, imposed by the exposure time given by:

$$C = (\text{undesirable illumination}) / (\text{total illumination})$$
$$= ((1/2) * t_{row}(t_{exp}/t_{row})((t_{exp}/t_{row}) - 1)) / (t_{exp} * N_{rows})$$
$$= ((t_{exp}/t_{row}) - 1) / (2 * N_{rows})$$

Embodiments of the present system may run in the limit on no crosstalk (texp=trow) with sufficient illumination and may depend on the losses in the optical systems and sensitivity of an imager used. The necessary exposure time may also depend on external factors, such as the allowable light flux to a patient to avoid undesirable heating and the field of view of an imaging system used.

Flat Illumination, Realistic Switching

In practice, the switching speed between different illumination conditions cannot be ignored and may be reduced (e.g., minimized) by using a Digital Micromirror Array (DMA) (also referred to as a Digital Micromirror Device (DMD)) In a DMA/DMD module of embodiments of the present system (e.g., a DLP LightCommander™, Logic PD) a maximum refresh rate is 5000 Hz, or $t_{refresh}$=200 μs. However, there is no need to rapidly switch back and forth between illumination conditions since lighting paths (e.g., path 1 CMBF-1 and light path 2 CMBF-2) are only being changed once per frame. Accordingly, a more relevant figure of merit in this case is an actual ON-OFF transition time for a DMA, which is on order 5 μs, or as a fraction of the row time, $t_{ON-OFF}/t_{row}$=6%. This implies that we can switch within a single row read time if the DMA is sufficiently synchronized with the imager (assuming, for example, the system is only limited by the jitter in the timing signal or other delays in the electronics). Additionally, even at full sensitivity, there will be Poisson noise from the photons. Given the sensor sensitivity, a full well may be estimated to be approximately 1000 e−, which implies a noise of $1/\sqrt{1000}$=3.16%. Thus, the system may be within a factor of two of this intrinsic noise floor.

Figure 7:
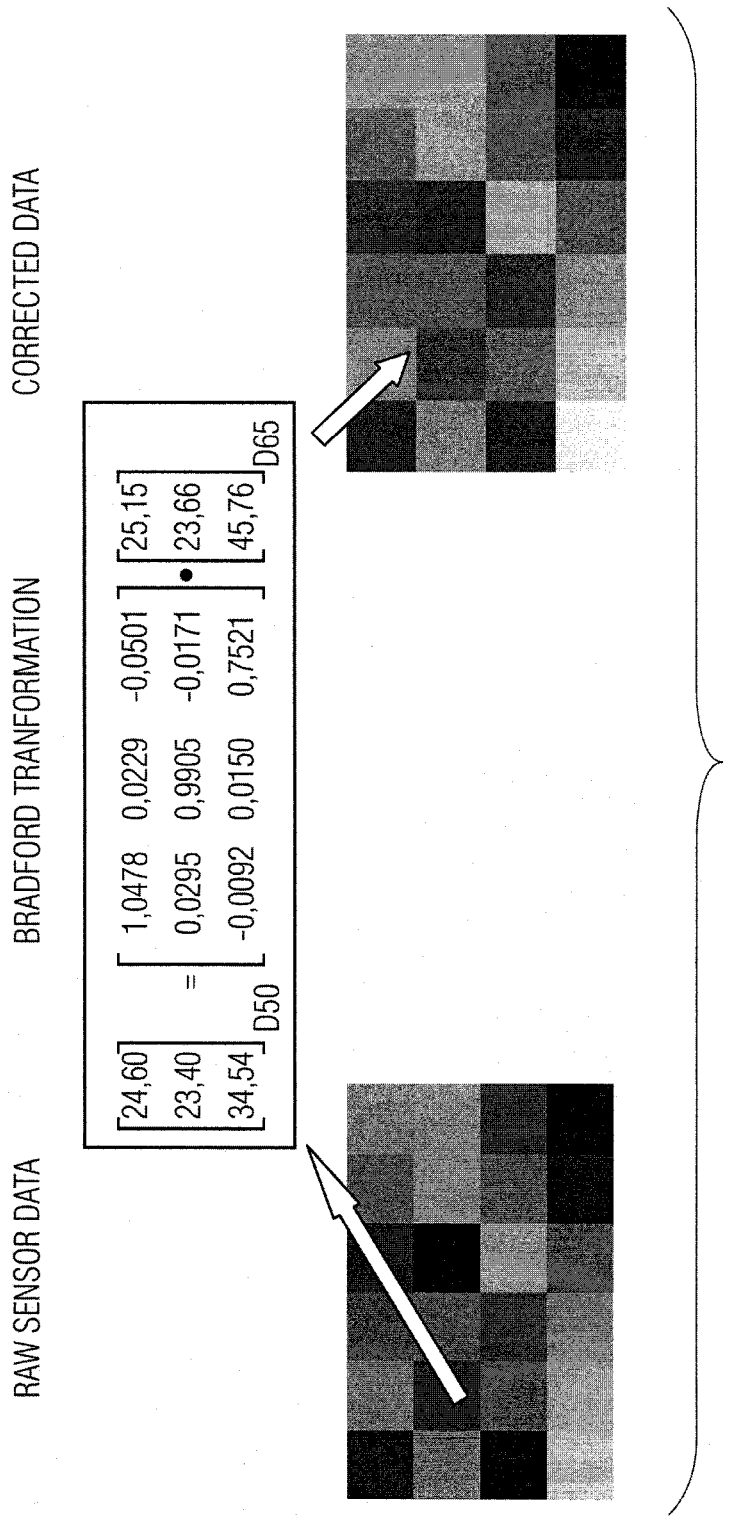
FIG. 7 is a graph of a correction matrix in accordance with embodiments of the present system.

FIG. 7 shows a graph of a correction matrix in accordance with embodiments of the present system. Raw information from the video out signal may be processed using any suitable processing methods such as a Bradford transformation.

FIG. 8 shows graphs 800A though 800D illustrating an application of a Bradford Matrix in accordance with embodiments of the present system. For example, the Bradford Matrix is used to determine a theoretical correction, where predicted measures values are generated based on the illumination condition, and the difference from a reference color checker chart is computed.

FIG. 9 shows a graph 900 illustrating error reduction after Bradford correction in accordance with embodiments of the present system.

FIG. 10 shows a graph 1000 of a histogram of error of left filters without chromatic adaptation in accordance with embodiments of the present system.

FIGS. 11A-C shows graphs 1100A through 1100C of spectral curves for error correction in accordance with embodiments of the present system.

FIG. 12 shows graphs 1200I through 1200E illustrating an error correction method in accordance with embodiments of the present system. Results are shown in Table 1200F.

FIG. 13 shows a schematic flow diagram 1300 of an image capture pipeline system available from Nvidia™ that may be used to capture 3D images for use along with the illumination systems in accordance with the present embodiments.

FIG. 14 shows a portion of a system 1400 (e.g., peer, server, etc.) in accordance with an embodiment of the present system. For example, a portion of the present system may include a processor 1410 operationally coupled to a memory 1420, a display 1430, RF transducers 1460, a camera/sensors 1490, and a user input device 1470. The memory 1420 may be any type of device for storing application data as well as other data related to the described operation. The application data and other data are received by the processor 1410 for configuring (e.g., programming) the processor 1410 to perform operation acts in accordance with the present system. The processor 1410 so configured becomes a special purpose machine or processor particularly suited for performing in accordance with embodiments of the present system.

The operation acts may include configuring an endoscopic imaging system by, for example, controlling one or more of a position of an imaging portion, the camera/sensors 1490, and/or the actuators 1460. The camera/sensors may provide information to the processor 1410 such as image information (in 2D or 3D), temperature information, position information, etc. The actuators 1460 may be controlled to position the camera in a desired orientation, turn the camera on/off, and/or to provide illumination to a volume of interest (VOI) so that the camera may capture images. The processor 1410 may receive the image information from the camera, and may render the image information on, for example, a user interface (UI) of the present system such as on the display 1430. Further, the processor 1410 may store the image information in a memory of the system such as the memory 1420 for later use.

The user input 1470 may include a joystick, a keyboard, a mouse, a trackball, or other device, such as a touch-sensitive display, which may be stand alone or be a part of a system, such as part of a personal computer, a personal digital assistant (PDA), a mobile phone, a monitor, a smart or dumb terminal or other device for communicating with the processor 1410 via any operable link. The user input device 1470 may be operable for interacting with the processor 1410 including enabling interaction within a UI as described herein. Clearly the processor 1410, the memory 1420, display 1430, and/or user input device 1470 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 1420 or other memory coupled to the processor 1410.

The program and/or program portions contained in the memory 1420 configure the processor 1410 to implement the methods, operational acts, and functions disclosed herein. The memories may be distributed, for example between the clients and/or servers, or local, and the processor 1410, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 1410. With this definition, information accessible through a network is still within the memory, for instance, because the processor 1410 may retrieve the information from the network for operation in accordance with the present system.

The processor 1410 is operable for providing control signals and/or performing operations in response to input signals from the user input device 1470 as well as in response to other devices of a network and executing instructions stored in the memory 1420. The processor 1410 may be an application-specific or general-use integrated circuit(s). Further, the processor 1410 may be a dedicated processor for performing in accordance with the present system or may be a general-purpose processor wherein only one of many functions operates for performing in accordance with the present system. The processor 1410 may operate utilizing a program portion, multiple program segments, or may be a hardware device utilizing a dedicated or multi-purpose integrated circuit. While the present system has been described with a reference to a gesture input system for manipulating a computer environment, it is also envisioned that user interaction with and/or manipulation of the computer environment may also be achieved using other devices such as a mouse, a trackball, a keyboard, a touch-sensitive display, a pointing device (e.g., a pen), a haptic device, etc.

Further variations of the present system would readily occur to a person of ordinary skill in the art and are encompassed by the following claims. Through operation of the present system, a virtual environment solicitation is provided to a user to enable simple immersion into a virtual environment and its objects.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. An endoscopic illumination system for illuminating a subject for stereoscopic image capture, the illumination system comprising:

a light source which outputs multi-spectral light;

first and second light paths configured to transmit the multi-spectral light;

a digital mirror array (DMA) which receives the multi-spectral light and directs the multi-spectral light to a selected one of the first and second light paths;

a controller which controls the DMA to direct the multi-spectral light to the selected light path in accordance with a time-multiplexing scheme;

a first complementary multiband bandpass filter (CMBF) and a second CMBF, the first CMBF being situated in the first light path and the second CMBF being situated in the second light path, wherein the first CMBF and the second CMBF filter the multi-spectral light incident thereupon to output filtered light; and a camera which captures video images of the subject and generates corresponding video information and a synchronization signal, the video information including a plurality of left and right image frame information, wherein the camera receives light reflected from the subject passing through a pupil CMBF pair and a detection lens, wherein the pupil CMBF pair includes a first pupil CMBF and a second pupil CMBF, the first pupil CMBF being identical to the first CMBF and the second pupil CMBF being identical to the second CMBF, and wherein the detection lens includes one unpartitioned section that covers both the first pupil CMBF and a second pupil CMBF, wherein the camera is located at a distal end of an endoscope for capturing the video images of a front view of the subject located in front direction of the endoscope, and wherein the camera is movable to provide a rear view which is opposite to the front view.

2. The endoscopic illumination system of claim 1, further comprising an optics portion which receives the multi-spectral light from the DMA and collimates the multi-spectral light which is to be incident on a selected CMBF of the first CMBF and the second CMBF.

3. The endoscopic illumination system of claim 1, further comprising transport optics which integrates the filtered light from at least one of the first CMBF and the second CMBF and transmits the filtered light along a third light path to illuminate the subject.

4. The endoscopic illumination system of claim 1, further comprising a synchronizer which determines a delay interval Δt in accordance with the plurality of left and right image frame information, and generates a trigger signal in accordance with the synchronization signal and the delay interval Δt for each of the left and right image frame information.

5. The endoscopic illumination system of claim 4, wherein the DMA controls timing of illumination to the selected path of the first and second light paths in accordance with the trigger signal.

6. An endoscopic illumination method for illuminating a subject for stereoscopic image capture, the illumination method controlled by a controller and comprising acts of:
outputting multi-spectral light by a light source;
selectively passing, using a digital mirror array (DMA), the multi-spectral light to a selected path of first and second light paths in accordance with a time-multiplexing scheme, the first light path having a first complementary multiband bandpass filter (CMBF) and the second light path having a second CMBF;
filtering, by a selected CMBF of the first CMBF or second CMBF, the multi-spectral light incident thereon and outputting filtered light;
illuminating the subject using the filtered light;
capturing video images of the subject; and
generating corresponding video information and a synchronization signal, the video information including a plurality of left and right image frame information, the synchronization signal corresponding to a start time of an act of capturing a left or a right image frame information of the plurality of left and right image frame information.

7. The endoscopic illumination method of claim 6, further comprising acts of:
receiving the multi-spectral light passed by the DMA; and
collimating the multi-spectral light which is to be incident on the selected first or second CMBFs of the optics portion.

8. The endoscopic illumination method of claim 6, further comprising acts of:
integrating the filtered light from the selected first or second CMBFs; and
transmitting the filtered light along a third light path to illuminate the subject.

9. The endoscopic illumination method of claim 6, further comprising acts of:
determining a delay interval Δt in accordance with the plurality of left and right image frame information; and
generating a trigger signal in accordance with the synchronization signal and the delay interval Δt for each of the left and right image frames.

10. The endoscopic illumination method of claim 9, further comprising an act of controlling timing of illumination to the selected one of the first and second light paths in accordance with the trigger signal.

11. A non-transitory computer readable medium embodying computer instructions to control illumination of a subject for stereoscopic image capture, wherein the computer instructions, when executed by a processor, configure the processor to control a system for performing the act of:
outputting, by a light source, multi-spectral light;
selectively passing, using a digital mirror array (DMA), the multi-spectral light to a selected path of first and second light paths in accordance with a time-multiplexing scheme, the first light path having a first complementary multiband bandpass filter (CMBF) and the second light path having a second CMBF;
filtering, by a selected CMBF of the first CMBF and the second CMBF, the multi-spectral light incident on the selected CMBF, and outputting filtered light;
illuminating the subject using the filtered light;
capturing video images of the subject; and
generating corresponding video information and a synchronization signal, the video information including a plurality of left and right image frame information, the synchronization signal corresponding to a start time of an act of capturing a left or a right image frame.

12. The non-transitory computer readable medium of claim 11, wherein the computer instructions further configure the processor to control the system for performing the act of:
receiving the multi-spectral light passed by the DMA; and
collimating the multi-spectral light which is to be incident on the selected first or second CMBFs of the optics portion for illuminating the subject through the selected first or second CMBFs for reflection from the subject and passage through a pupil CMBF pair and a detection lens for detection by a detector, wherein the pupil CMBF is identical to the selected first or second CMBFs, wherein the pupil CMBF pair includes a first pupil CMBF and a second pupil CMBF, and wherein the detection lens includes one section that covers both the first pupil CMBF and a second pupil CMBF.

13. The non-transitory computer readable medium of claim 11, wherein the computer instructions further configure the processor to control the system for performing the act of:
integrating the filtered light from the selected first or second CMBFs; and
transmitting the filtered light along a third light path to illuminate the subject.

14. The non-transitory computer readable medium of claim 11, wherein the computer instructions further configure the processor to control the system for performing the act of:
determining a delay interval Δt in accordance with the plurality of left and right image frame information; and
generating a trigger signal in accordance with the synchronization signal and the delay interval Δt for each of the left and right image frames.

15. The non-transitory computer readable medium of claim 14, wherein the computer instructions further configure the processor to control the system for performing the act of controlling timing of illumination to the selected path of the first or the second light paths in accordance with the trigger signal.

16. An endoscopic illumination system for illuminating a subject for stereoscopic image capture, the illumination system comprising:
a light source which outputs multi-spectral light;
a dispersive optical element which spatially separates wavelengths of the multi-spectral light;

a digital mirror array (DMA) which receives the spatially separated wavelengths and passes selected wavelengths of the spatially separated wavelengths to a light path; and a controller which controls the DMA to pass the selected wavelengths in accordance with a time-multiplexing scheme; and a camera which captures video images of the subject and generates corresponding video information and a synchronization signal, the video information including a plurality of left and right image frame information, wherein the camera receives light reflected from the subject passing through a pupil complementary multiband bandpass filter (CMBF) pair and a detection lens, wherein the pupil CMBF pair includes a first pupil CMBF and a second pupil CMBF, wherein the detection lens includes one unpartitioned section that covers both the first pupil CMBF and a second pupil CMBF, wherein the camera is located at a distal end of an endoscope for capturing the video images of a front view of the subject located in a front direction of the endoscope, and wherein the camera is movable to provide a further view which is different from the front view.

17. The endoscopic illumination system of claim 16, wherein the dispersive optical element comprises a prism or a grating.

18. An endoscopic system for illuminating a subject for stereoscopic image capture, the illumination system comprising:

a processor; and
a memory operatively coupled to the processor,
wherein the processor is configured to:
cause a light source to output multi-spectral light;
cause a digital mirror array (DMA) to selectively pass the multi-spectral light to a selected path of first and second light paths in accordance with a time-multiplexing scheme, the first light path having a first complementary multiband bandpass filter (CMBF) and the second light path having a second CMB for filtering, by a selected CMBF of the first CMBF or second CMBF, the multi-spectral light incident thereon and outputting filtered light for illuminating the subject using the filtered light;
cause a camera to capture video images of the subject; and
cause generation of corresponding video information and a synchronization signal, the video information including a plurality of left and right image frame information, the synchronization signal corresponding to a start time of an act of capturing a left or a right image frame information of the plurality of left and right image frame information.

19. The endoscopic system of claim 18, further comprising an optics portion which receives the multi-spectral light from the DMA and collimates the multi-spectral light which is to be incident on a selected CMBF of the first CMBF and the second CMBF.

20. The endoscopic system of claim 18, further comprising transport optics which integrates the filtered light from at least one of the first CMBF and the second CMBF and transmits the filtered light along a third light path to illuminate the subject.

* * * * *